(12) United States Patent
Nobles

(10) Patent No.: US 11,202,624 B2
(45) Date of Patent: Dec. 21, 2021

(54) APPARATUS FOR APPLYING A KNOT TO A SUTURE

(71) Applicant: Nobles Medical Technologies II, Inc., Fountain Valley, CA (US)

(72) Inventor: Anthony A. Nobles, St. Thomas, VI (US)

(73) Assignee: Nobles Medical Technologies II, Inc., Fountain Valley, CA (US)

( * ) Notice: Subject to any disclaimer, the term of this patent is extended or adjusted under 35 U.S.C. 154(b) by 123 days.

(21) Appl. No.: 16/790,420

(22) Filed: Feb. 13, 2020

(65) Prior Publication Data

US 2020/0289108 A1   Sep. 17, 2020

Related U.S. Application Data

(63) Continuation of application No. PCT/IB2018/056250, filed on Aug. 17, 2018.

(60) Provisional application No. 62/547,717, filed on Aug. 18, 2017.

(51) Int. Cl.
*A61B 17/04* (2006.01)
*A61B 17/00* (2006.01)

(52) U.S. Cl.
CPC ...... *A61B 17/0469* (2013.01); *A61B 17/0467* (2013.01); *A61B 2017/00407* (2013.01); *A61B 2017/0474* (2013.01)

(58) Field of Classification Search
CPC ............ A61B 17/0467; A61B 17/0469; A61B 17/0485; A61B 17/0487; A61B 2017/00243; A61B 2017/00371; A61B 2017/00407; A61B 2017/00477; A61B 2017/0488; A61B 2017/0474; A61B 2090/0811
See application file for complete search history.

(56) References Cited

U.S. PATENT DOCUMENTS

| | | |
|---|---|---|
| 118,683 A | 9/1871 | Bruce |
| 1,064,307 A | 6/1913 | Fleming |
| 1,822,330 A | 9/1931 | Ainslie |

(Continued)

FOREIGN PATENT DOCUMENTS

| | | |
|---|---|---|
| CN | 101495049 | 12/2010 |
| CN | 101257852 | 8/2011 |

(Continued)

OTHER PUBLICATIONS

Advances in Vascular Surgery, by John S. Najarian, M.D. and John P. Delaney, M.D., copyright 1983 by Year Book Publishers, Inc. at pp. 94,95,96, and 224.

(Continued)

*Primary Examiner* — Jocelin C Tanner
(74) *Attorney, Agent, or Firm* — Knobbe, Martens, Olson & Bear LLP

(57) ABSTRACT

Knot placement devices and methods can improve the ease for a user and/or success of ejecting a knot having a knot body and a plug, cutting suture and/or releasing the cut suture. The knot placement device can have an incremental rotational feature to cut the suture. The knot placement device can include first and second actuators configured for forming and ejecting a knot. The second actuator can be reversed in its position to release suture(s) caught within the device.

20 Claims, 24 Drawing Sheets

(56) References Cited

U.S. PATENT DOCUMENTS

| | | |
|---|---|---|
| 1,989,919 A | 2/1935 | Everitt |
| 2,348,218 A | 5/1944 | Karle |
| 2,473,742 A | 6/1949 | Auzin |
| 2,548,602 A | 4/1951 | Greenburg |
| 2,637,290 A | 5/1953 | Sigoda |
| 2,738,790 A | 3/1956 | Todt, Sr. et al. |
| 2,849,002 A | 8/1958 | Oddo |
| 2,945,460 A | 7/1960 | Kagiyama |
| 3,241,554 A | 3/1966 | Coanda |
| 3,292,627 A | 12/1966 | Harautuneian |
| 3,394,705 A | 7/1968 | Abramson |
| 3,664,345 A | 5/1972 | Dabbs et al. |
| 3,665,926 A | 5/1972 | Flores |
| 3,774,596 A | 11/1973 | Cook |
| 3,828,790 A | 8/1974 | Curtiss et al. |
| 3,831,587 A | 8/1974 | Boyd |
| 3,842,840 A | 10/1974 | Schweizer |
| 3,877,434 A | 4/1975 | Ferguson et al. |
| 3,882,852 A | 5/1975 | Sinnreich |
| 3,882,855 A | 5/1975 | Schulte et al. |
| 3,888,117 A | 6/1975 | Lewis |
| 3,903,893 A | 9/1975 | Scheer |
| 3,946,740 A | 3/1976 | Bassett |
| 3,946,741 A | 3/1976 | Adair |
| 3,952,742 A | 4/1976 | Taylor |
| 3,976,079 A | 8/1976 | Samuels |
| 4,052,980 A | 10/1977 | Grams et al. |
| RE29,703 E | 7/1978 | Fatt |
| 4,107,953 A | 8/1978 | Casillo |
| 4,119,100 A | 10/1978 | Rickett |
| 4,164,225 A | 8/1979 | Johnson et al. |
| 4,230,119 A | 10/1980 | Blum |
| 4,291,698 A | 9/1981 | Fuchs et al. |
| 4,299,237 A | 11/1981 | Foti |
| 4,307,722 A | 12/1981 | Evans |
| 4,345,601 A | 8/1982 | Fukuda |
| 4,351,342 A | 9/1982 | Wiita et al. |
| 4,417,532 A | 11/1983 | Yasukata |
| 4,423,725 A | 1/1984 | Baran et al. |
| 4,447,227 A | 5/1984 | Kotsanis |
| 4,457,300 A | 7/1984 | Budde |
| 4,484,580 A | 11/1984 | Nomoto et al. |
| 4,512,338 A | 4/1985 | Balko et al. |
| 4,546,759 A | 10/1985 | Solar |
| 4,553,543 A | 11/1985 | Amarasinghe |
| 4,573,966 A | 3/1986 | Weikl et al. |
| 4,589,868 A | 5/1986 | Dretler |
| 4,610,662 A | 9/1986 | Weikl et al. |
| 4,617,738 A | 10/1986 | Kopacz |
| 4,662,068 A | 5/1987 | Polonsky |
| 4,664,114 A | 5/1987 | Ghodsian |
| 4,734,094 A | 3/1988 | Jacob et al. |
| 4,744,364 A | 5/1988 | Kensey |
| 4,750,492 A | 6/1988 | Jacobs |
| 4,771,776 A | 9/1988 | Powell et al. |
| 4,774,091 A | 9/1988 | Yamahira et al. |
| 4,794,928 A | 1/1989 | Kletschka |
| 4,795,427 A | 1/1989 | Helzel |
| 4,796,629 A | 1/1989 | Grayzel |
| 4,824,436 A | 4/1989 | Wolinsky |
| 4,827,931 A | 5/1989 | Longmore |
| 4,841,888 A | 6/1989 | Mills et al. |
| 4,861,330 A | 8/1989 | Voss |
| 4,898,168 A | 2/1990 | Yule |
| 4,923,461 A | 5/1990 | Caspari et al. |
| 4,926,860 A | 5/1990 | Stice et al. |
| 4,932,956 A | 6/1990 | Reddy et al. |
| 4,935,027 A | 6/1990 | Yoon |
| 4,954,126 A | 9/1990 | Wallsten |
| 4,957,498 A | 9/1990 | Caspari et al. |
| 4,972,845 A | 11/1990 | Iversen et al. |
| 4,981,149 A | 1/1991 | Yoon et al. |
| 4,983,116 A | 1/1991 | Koga |
| 4,984,564 A | 1/1991 | Yuen |
| 4,994,070 A | 2/1991 | Waters |
| 5,002,531 A | 3/1991 | Bonzel |
| 5,021,059 A | 6/1991 | Kensey et al. |
| 5,037,433 A | 8/1991 | Wilk et al. |
| 5,057,114 A | 10/1991 | Wittich et al. |
| 5,059,201 A | 10/1991 | Asnis |
| 5,065,772 A | 11/1991 | Cox, Jr. |
| 5,074,871 A | 12/1991 | Groshong |
| 5,078,743 A | 1/1992 | Mikalov et al. |
| 5,090,958 A | 2/1992 | Sahota |
| 5,100,418 A | 3/1992 | Yoon et al. |
| 5,104,394 A | 4/1992 | Knoepfler |
| 5,106,363 A | 4/1992 | Nobuyoshi |
| 5,108,416 A | 4/1992 | Ryan et al. |
| 5,108,419 A | 4/1992 | Reger et al. |
| 5,116,305 A | 5/1992 | Milder et al. |
| 5,122,122 A | 6/1992 | Allgood |
| 5,129,883 A | 7/1992 | Black |
| 5,133,724 A | 7/1992 | Wilson et al. |
| 5,135,484 A | 8/1992 | Wright |
| 5,160,339 A | 11/1992 | Chen et al. |
| 5,163,906 A | 11/1992 | Ahmadi |
| 5,167,223 A | 12/1992 | Koros et al. |
| 5,171,251 A | 12/1992 | Bregen et al. |
| 5,176,691 A | 1/1993 | Pierce |
| 5,192,301 A | 3/1993 | Kamiya et al. |
| 5,222,508 A | 6/1993 | Contarini |
| 5,222,941 A | 6/1993 | Don Michael |
| 5,222,974 A | 6/1993 | Kensey et al. |
| 5,224,948 A | 7/1993 | Abe et al. |
| 5,236,443 A | 8/1993 | Sontag |
| 5,242,459 A | 9/1993 | Buelna |
| 5,281,234 A | 1/1994 | Wilk et al. |
| 5,281,237 A | 1/1994 | Gimpelson |
| 5,282,827 A | 2/1994 | Kensey et al. |
| 5,286,259 A | 2/1994 | Ganguly et al. |
| 5,290,249 A | 3/1994 | Foster et al. |
| 5,291,639 A | 3/1994 | Baum et al. |
| 5,300,106 A | 4/1994 | Dahl et al. |
| 5,304,184 A | 4/1994 | Hathaway et al. |
| 5,308,323 A | 5/1994 | Sogawa et al. |
| 5,312,344 A | 5/1994 | Grinfeld |
| 5,314,409 A | 5/1994 | Sarosiek et al. |
| 5,320,604 A | 6/1994 | Walker et al. |
| 5,320,632 A | 6/1994 | Heidmueller |
| 5,330,446 A | 7/1994 | Weldon et al. |
| 5,330,497 A | 7/1994 | Freitas et al. |
| 5,331,975 A | 7/1994 | Bonutti |
| 5,336,229 A | 8/1994 | Noda |
| 5,336,231 A | 8/1994 | Adair |
| 5,337,736 A | 8/1994 | Reddy |
| 5,339,801 A | 8/1994 | Poloyko |
| 5,342,306 A | 8/1994 | Don Michael |
| 5,342,385 A | 8/1994 | Norelli et al. |
| 5,342,393 A | 8/1994 | Stack |
| 5,350,399 A | 9/1994 | Erlebacher et al. |
| 5,356,382 A | 10/1994 | Picha et al. |
| 5,364,407 A | 11/1994 | Poll |
| 5,364,408 A | 11/1994 | Gordon |
| 5,368,601 A | 11/1994 | Sauer et al. |
| 5,370,618 A | 12/1994 | Leonhardt |
| 5,370,685 A | 12/1994 | Stevens |
| 5,374,275 A | 12/1994 | Bradley et al. |
| 5,380,284 A | 1/1995 | Don Michael |
| 5,382,261 A | 1/1995 | Palmaz |
| 5,383,854 A | 1/1995 | Safar et al. |
| 5,383,896 A | 1/1995 | Gershony et al. |
| 5,383,897 A | 1/1995 | Wholey |
| 5,383,905 A | 1/1995 | Golds et al. |
| 5,389,103 A | 2/1995 | Melzer et al. |
| 5,391,147 A | 2/1995 | Imran et al. |
| 5,391,174 A | 2/1995 | Weston |
| 5,395,383 A | 3/1995 | Adams et al. |
| 5,397,325 A | 3/1995 | Badia et al. |
| 5,403,329 A | 4/1995 | Hinchcliffe |
| 5,403,331 A | 4/1995 | Chesterfield et al. |
| 5,403,341 A | 4/1995 | Solar |
| 5,405,322 A | 4/1995 | Lennox et al. |
| 5,405,354 A | 4/1995 | Sarrett |
| 5,417,699 A | 5/1995 | Klein et al. |

(56) References Cited

U.S. PATENT DOCUMENTS

| | | |
|---|---|---|
| 5,417,700 A | 5/1995 | Egan |
| 5,423,777 A | 6/1995 | Tajiri et al. |
| 5,423,837 A | 6/1995 | Mericle et al. |
| 5,425,708 A | 6/1995 | Nasu |
| 5,425,737 A | 6/1995 | Burbank et al. |
| 5,425,744 A | 6/1995 | Fagan et al. |
| 5,429,118 A | 7/1995 | Cole et al. |
| 5,431,666 A | 7/1995 | Sauer et al. |
| 5,439,470 A | 8/1995 | Li |
| 5,445,167 A | 8/1995 | Yoon et al. |
| 5,447,515 A | 9/1995 | Robicsek |
| 5,452,513 A | 9/1995 | Zinnbauer et al. |
| 5,454,823 A | 10/1995 | Richardson et al. |
| 5,458,574 A | 10/1995 | Machold et al. |
| 5,458,609 A | 10/1995 | Gordon et al. |
| 5,462,560 A | 10/1995 | Stevens |
| 5,462,561 A | 10/1995 | Voda |
| 5,470,338 A | 11/1995 | Whitefield et al. |
| 5,474,572 A | 12/1995 | Hayburst |
| 5,476,469 A | 12/1995 | Hathaway et al. |
| 5,476,470 A | 12/1995 | Fitzgibbons, Jr. |
| 5,496,332 A | 3/1996 | Sierra et al. |
| 5,499,991 A | 3/1996 | Garman et al. |
| 5,501,691 A | 3/1996 | Goldrath |
| 5,507,754 A | 4/1996 | Green et al. |
| 5,507,755 A | 4/1996 | Gresl et al. |
| 5,514,159 A | 5/1996 | Matula et al. |
| 5,520,609 A | 5/1996 | Moll et al. |
| 5,520,702 A | 5/1996 | Sauer et al. |
| 5,522,961 A | 6/1996 | Leonhardt |
| 5,527,321 A | 6/1996 | Hinchliffe |
| 5,527,322 A | 6/1996 | Klein et al. |
| 5,527,338 A | 6/1996 | Purdy |
| 5,540,658 A | 7/1996 | Evans et al. |
| 5,540,704 A | 7/1996 | Gordon et al. |
| 5,545,170 A | 8/1996 | Hart |
| 5,549,633 A | 8/1996 | Evans et al. |
| 5,558,642 A | 9/1996 | Schweich et al. |
| 5,558,644 A | 9/1996 | Boyd et al. |
| RE35,352 E | 10/1996 | Peters |
| 5,562,686 A | 10/1996 | Sauer et al. |
| 5,562,688 A | 10/1996 | Riza |
| 5,565,122 A | 10/1996 | Zinnbauer et al. |
| 5,571,090 A | 11/1996 | Sherts |
| 5,573,540 A | 11/1996 | Yoon |
| 5,584,835 A | 12/1996 | Greenfield |
| 5,584,861 A | 12/1996 | Swain et al. |
| 5,591,195 A | 1/1997 | Taheri et al. |
| 5,593,422 A | 1/1997 | Muijs Van de Moer et al. |
| 5,599,307 A | 2/1997 | Bacher et al. |
| 5,603,718 A | 2/1997 | Xu |
| 5,613,974 A | 3/1997 | Andreas et al. |
| 5,613,975 A | 3/1997 | Christy |
| 5,626,590 A | 5/1997 | Wilk |
| 5,630,833 A | 5/1997 | Katsaros et al. |
| 5,632,751 A | 5/1997 | Piraka |
| 5,632,752 A | 5/1997 | Buelna |
| 5,634,936 A | 6/1997 | Linden et al. |
| 5,637,097 A | 6/1997 | Yoon |
| 5,643,289 A | 7/1997 | Sauer et al. |
| 5,645,553 A | 7/1997 | Kolesa et al. |
| 5,662,663 A | 9/1997 | Shallman |
| 5,669,917 A | 9/1997 | Sauer et al. |
| 5,669,971 A | 9/1997 | Bok et al. |
| 5,674,198 A | 10/1997 | Leone |
| 5,681,296 A | 10/1997 | Ishida |
| 5,681,351 A | 10/1997 | Jamiolkowski et al. |
| 5,688,245 A | 11/1997 | Runge |
| 5,690,674 A | 11/1997 | Diaz |
| 5,695,468 A | 12/1997 | Lafontaine et al. |
| 5,695,504 A | 12/1997 | Gifford, III et al. |
| 5,697,905 A | 12/1997 | D'Amnbrosio |
| 5,700,273 A | 12/1997 | Buelna et al. |
| 5,700,277 A | 12/1997 | Nash et al. |
| 5,707,379 A | 1/1998 | Fleenor et al. |
| 5,709,693 A | 1/1998 | Taylor |
| 5,716,329 A | 2/1998 | Dieter |
| 5,720,757 A | 2/1998 | Hathaway et al. |
| 5,722,983 A | 3/1998 | Van Der Weegen |
| 5,728,109 A | 3/1998 | Schulze et al. |
| 5,738,629 A | 4/1998 | Moll et al. |
| 5,743,852 A | 4/1998 | Johnson |
| 5,746,753 A | 5/1998 | Sullivan et al. |
| 5,749,883 A | 5/1998 | Halpern |
| 5,759,188 A | 6/1998 | Yoon |
| 5,766,183 A | 6/1998 | Sauer |
| 5,766,220 A | 6/1998 | Moenning |
| 5,769,870 A | 6/1998 | Salahieh et al. |
| 5,779,719 A | 7/1998 | Klein et al. |
| 5,792,152 A | 8/1998 | Klein et al. |
| 5,792,153 A | 8/1998 | Swain et al. |
| 5,795,289 A | 8/1998 | Wyttenbach |
| 5,795,325 A | 8/1998 | Valley et al. |
| 5,797,948 A | 8/1998 | Dunham |
| 5,797,960 A | 8/1998 | Stevens et al. |
| 5,810,757 A | 9/1998 | Sweezer et al. |
| 5,810,849 A | 9/1998 | Kontos |
| 5,810,850 A | 9/1998 | Hathaway et al. |
| 5,817,108 A | 10/1998 | Poncet |
| 5,817,110 A | 10/1998 | Kronner |
| 5,820,631 A | 10/1998 | Nobles |
| 5,836,955 A | 11/1998 | Buelna et al. |
| 5,843,100 A | 12/1998 | Meade |
| 5,846,251 A | 12/1998 | Hart |
| 5,846,253 A | 12/1998 | Buelna et al. |
| 5,853,399 A | 12/1998 | Sasaki |
| 5,853,422 A | 12/1998 | Huebsch et al. |
| 5,855,585 A | 1/1999 | Kontos |
| 5,860,990 A | 1/1999 | Nobles et al. |
| 5,860,991 A | 1/1999 | Klein et al. |
| 5,860,992 A | 1/1999 | Daniel et al. |
| 5,860,997 A | 1/1999 | Bonutti |
| 5,861,003 A | 1/1999 | Latson et al. |
| 5,865,729 A | 2/1999 | Meehan et al. |
| 5,868,708 A | 2/1999 | Hart et al. |
| 5,868,762 A | 2/1999 | Cragg et al. |
| 5,871,320 A | 2/1999 | Kovac |
| 5,871,537 A | 2/1999 | Holman et al. |
| 5,876,411 A | 3/1999 | Kontos |
| 5,899,921 A | 5/1999 | Caspari et al. |
| 5,902,311 A | 5/1999 | Andreas et al. |
| 5,902,321 A | 5/1999 | Caspari et al. |
| 5,906,577 A | 5/1999 | Beane et al. |
| 5,908,428 A | 6/1999 | Scirica et al. |
| 5,919,200 A | 7/1999 | Stambaugh et al. |
| 5,919,208 A | 7/1999 | Valenti |
| 5,928,192 A | 7/1999 | Maahs |
| 5,931,844 A | 8/1999 | Thompson et al. |
| 5,935,098 A | 8/1999 | Blaisdell et al. |
| 5,935,149 A | 8/1999 | Ek |
| 5,944,730 A | 8/1999 | Nobles et al. |
| 5,951,588 A | 9/1999 | Moenning |
| 5,951,590 A | 9/1999 | Goldfarb |
| 5,954,732 A | 9/1999 | Hart et al. |
| 5,967,970 A | 10/1999 | Cowan et al. |
| 5,971,983 A | 10/1999 | Lesh |
| 5,972,005 A | 10/1999 | Stalker et al. |
| 5,980,539 A | 11/1999 | Kontos |
| 5,993,466 A | 11/1999 | Yoon |
| 5,997,555 A | 12/1999 | Kontos |
| 6,001,109 A | 12/1999 | Kontos |
| 6,004,337 A | 12/1999 | Kieturakis et al. |
| 6,010,530 A | 1/2000 | Goicoechea |
| 6,015,428 A | 1/2000 | Pagedas |
| 6,024,747 A | 2/2000 | Kontos |
| 6,033,430 A | 3/2000 | Bonutti |
| 6,036,699 A | 3/2000 | Andreas et al. |
| 6,059,800 A | 5/2000 | Hart et al. |
| 6,066,160 A | 5/2000 | Colvin et al. |
| 6,068,648 A | 5/2000 | Cole et al. |
| 6,071,271 A | 6/2000 | Baker et al. |
| 6,077,277 A | 6/2000 | Mollenauer et al. |
| 6,086,608 A | 7/2000 | Ek et al. |
| 6,099,553 A | 8/2000 | Hart et al. |

(56) References Cited

U.S. PATENT DOCUMENTS

| | | | |
|---|---|---|---|
| 6,110,185 A | 8/2000 | Barra et al. |
| 6,113,580 A | 9/2000 | Dolisi |
| 6,117,144 A | 9/2000 | Nobles et al. |
| 6,126,677 A | 10/2000 | Ganaja et al. |
| 6,136,010 A | 10/2000 | Modesitt et al. |
| 6,143,015 A | 11/2000 | Nobles |
| 6,159,234 A | 12/2000 | Bonutti et al. |
| 6,171,319 B1 | 1/2001 | Nobles et al. |
| 6,174,324 B1 | 1/2001 | Egan et al. |
| 6,187,026 B1 | 2/2001 | Devlin et al. |
| 6,190,396 B1 | 2/2001 | Whitin et al. |
| 6,200,329 B1 | 3/2001 | Fung et al. |
| 6,203,565 B1 | 3/2001 | Bonutti et al. |
| 6,210,429 B1 | 4/2001 | Vardi et al. |
| 6,217,591 B1 | 4/2001 | Egan et al. |
| 6,241,699 B1 | 6/2001 | Suresh et al. |
| 6,245,079 B1 | 6/2001 | Nobles et al. |
| 6,245,080 B1 | 6/2001 | Levinson |
| 6,248,121 B1 | 6/2001 | Nobles |
| 6,254,620 B1 * | 7/2001 | Koh .............. A61B 17/0467 30/278 |
| 6,280,460 B1 | 8/2001 | Bolduc et al. |
| 6,290,674 B1 | 9/2001 | Roue et al. |
| 6,332,889 B1 | 12/2001 | Sancoff et al. |
| 6,348,059 B1 | 2/2002 | Hathaway et al. |
| 6,352,543 B1 | 3/2002 | Cole et al. |
| 6,383,208 B1 | 5/2002 | Sancoff et al. |
| 6,395,015 B1 | 5/2002 | Borst et al. |
| 6,409,739 B1 | 6/2002 | Nobles et al. |
| 6,432,115 B1 | 8/2002 | Mollenauer et al. |
| 6,468,293 B2 | 10/2002 | Bonutti et al. |
| 6,508,777 B1 | 1/2003 | Macoviak et al. |
| 6,527,785 B2 | 3/2003 | Sancoff et al. |
| 6,533,795 B1 | 3/2003 | Tran et al. |
| 6,537,299 B1 | 3/2003 | Hogendijk et al. |
| 6,547,725 B1 | 4/2003 | Paolitto et al. |
| 6,547,760 B1 | 4/2003 | Samson et al. |
| 6,551,331 B2 | 4/2003 | Nobles et al. |
| 6,562,052 B2 | 5/2003 | Nobles et al. |
| 6,585,689 B1 | 7/2003 | Macoviak et al. |
| 6,663,643 B2 | 12/2003 | Field et al. |
| 6,679,895 B1 | 1/2004 | Sancoff et al. |
| 6,682,540 B1 | 1/2004 | Sancoff et al. |
| 6,716,243 B1 | 4/2004 | Colvin et al. |
| 6,726,651 B1 | 4/2004 | Robinson et al. |
| 6,733,509 B2 | 5/2004 | Nobles et al. |
| 6,767,352 B2 | 7/2004 | Field et al. |
| 6,770,076 B2 | 8/2004 | Foerster |
| 6,770,084 B1 | 8/2004 | Bain et al. |
| 6,786,913 B2 | 9/2004 | Sancoff |
| 6,978,176 B2 | 1/2005 | Lattouf |
| 6,855,157 B2 | 2/2005 | Foerster et al. |
| 6,893,448 B2 | 5/2005 | O'Quinn et al. |
| 6,911,034 B2 | 6/2005 | Nobles et al. |
| 6,913,600 B2 | 7/2005 | Valley et al. |
| 6,936,057 B1 | 8/2005 | Nobles |
| 7,004,952 B2 | 2/2006 | Nobles et al. |
| 7,083,630 B2 | 8/2006 | DeVries et al. |
| 7,083,638 B2 | 8/2006 | Foerster |
| 7,090,686 B2 | 8/2006 | Nobles et al. |
| 7,090,690 B2 | 8/2006 | Foerster et al. |
| 7,118,583 B2 | 10/2006 | O'Quinn et al. |
| 7,160,309 B2 | 1/2007 | Voss |
| 7,172,595 B1 | 2/2007 | Goble |
| 7,220,266 B2 | 5/2007 | Gambale |
| 7,232,446 B1 | 6/2007 | Farris |
| 7,235,086 B2 | 6/2007 | Sauer et al. |
| 7,326,221 B2 | 2/2008 | Sakamoto et al. |
| 7,329,272 B2 | 2/2008 | Burkhart et al. |
| 7,338,502 B2 | 3/2008 | Rosenblatt |
| 7,381,210 B2 | 6/2008 | Zarbatany et al. |
| 7,399,304 B2 | 7/2008 | Gambale et al. |
| 7,435,251 B2 | 10/2008 | Green |
| 7,449,024 B2 | 11/2008 | Stafford |
| 7,491,217 B1 | 2/2009 | Hendren |
| 7,601,161 B1 | 10/2009 | Nobles et al. |
| 7,628,797 B2 | 12/2009 | Tieu et al. |
| 7,635,386 B1 | 12/2009 | Gammie |
| 7,637,926 B2 | 12/2009 | Foerster et al. |
| 7,722,629 B2 | 5/2010 | Chambers |
| 7,803,167 B2 | 9/2010 | Nobles et al. |
| 7,842,051 B2 | 11/2010 | Dana et al. |
| 7,846,181 B2 | 12/2010 | Schwartz et al. |
| 7,879,072 B2 | 2/2011 | Bonutti et al. |
| 7,905,892 B2 | 3/2011 | Nobles et al. |
| 7,918,867 B2 | 4/2011 | Dana et al. |
| 7,931,641 B2 | 4/2011 | Chang et al. |
| 7,993,368 B2 | 8/2011 | Gambale et al. |
| 8,075,573 B2 | 12/2011 | Gambale et al. |
| 8,083,754 B2 | 12/2011 | Pantages et al. |
| 8,105,355 B2 | 1/2012 | Page et al. |
| 8,197,497 B2 | 6/2012 | Nobles et al. |
| 8,202,281 B2 | 6/2012 | Voss |
| 8,246,636 B2 | 8/2012 | Nobles et al. |
| 8,252,005 B2 | 8/2012 | Findlay, III et al. |
| 8,282,659 B2 | 10/2012 | Oren et al. |
| 8,287,556 B2 | 10/2012 | Gilkey et al. |
| 8,298,291 B2 | 10/2012 | Ewers et al. |
| 8,303,622 B2 | 11/2012 | Alkhatib |
| 8,348,962 B2 | 1/2013 | Nobles et al. |
| 8,372,089 B2 | 2/2013 | Nobles et al. |
| 8,398,676 B2 | 3/2013 | Roorda et al. |
| 8,430,893 B2 | 4/2013 | Ma |
| 8,469,975 B2 | 6/2013 | Nobles et al. |
| 8,496,676 B2 | 7/2013 | Nobles et al. |
| 8,500,776 B2 | 8/2013 | Ebner |
| 8,540,736 B2 | 9/2013 | Gaynor et al. |
| 8,568,427 B2 | 10/2013 | Nobles et al. |
| 8,623,036 B2 | 1/2014 | Harrison et al. |
| 8,728,105 B2 | 5/2014 | Aguirre |
| 8,758,370 B2 | 6/2014 | Shikhman et al. |
| 8,771,296 B2 | 7/2014 | Nobles et al. |
| 9,131,938 B2 | 9/2015 | Nobles et al. |
| 9,326,764 B2 | 5/2016 | Nobles et al. |
| 9,332,976 B2 | 5/2016 | Yribarren |
| 9,364,238 B2 | 6/2016 | Bakos et al. |
| 9,398,907 B2 | 7/2016 | Nobles et al. |
| 9,402,605 B2 | 8/2016 | Viola |
| 9,649,106 B2 | 5/2017 | Nobles et al. |
| 9,706,988 B2 | 7/2017 | Nobles et al. |
| 10,178,993 B2 | 1/2019 | Nobles et al. |
| 10,182,802 B2 | 1/2019 | Nobles et al. |
| 10,194,902 B2 | 2/2019 | Nobles et al. |
| 10,285,687 B2 | 5/2019 | Nobles et al. |
| 10,420,545 B2 | 9/2019 | Nobles et al. |
| 10,512,458 B2 | 12/2019 | Nobles |
| 10,610,216 B2 | 4/2020 | Nobles et al. |
| 10,624,629 B2 | 4/2020 | Nobles et al. |
| 2001/0031973 A1 | 10/2001 | Nobles et al. |
| 2002/0013601 A1 | 1/2002 | Nobles et al. |
| 2002/0045908 A1 | 4/2002 | Nobles et al. |
| 2002/0049453 A1 | 4/2002 | Nobles et al. |
| 2002/0096183 A1 | 7/2002 | Stevens et al. |
| 2002/0128598 A1 | 9/2002 | Nobles |
| 2002/0169475 A1 | 11/2002 | Gainor et al. |
| 2002/0183787 A1 | 12/2002 | Wahr et al. |
| 2003/0078601 A1 | 4/2003 | Skikhman et al. |
| 2003/0114863 A1 | 6/2003 | Field et al. |
| 2003/0120287 A1 * | 6/2003 | Gross ............ A61B 17/0469 606/148 |
| 2003/0144673 A1 | 7/2003 | Onuki et al. |
| 2003/0204205 A1 | 10/2003 | Sauer et al. |
| 2003/0208209 A1 | 11/2003 | Gambale et al. |
| 2003/0220667 A1 | 11/2003 | van der Burg et al. |
| 2004/0015177 A1 | 1/2004 | Chu |
| 2004/0044365 A1 | 3/2004 | Bachman |
| 2004/0059351 A1 | 3/2004 | Eigler et al. |
| 2004/0102797 A1 | 5/2004 | Golden et al. |
| 2004/0153116 A1 | 8/2004 | Nobles |
| 2004/0236356 A1 | 11/2004 | Rioux et al. |
| 2004/0260298 A1 | 12/2004 | Kaiseer et al. |
| 2005/0033361 A1 | 2/2005 | Galdonik et al. |
| 2005/0070923 A1 | 3/2005 | McIntosh |
| 2005/0149066 A1 | 7/2005 | Stafford |

(56) References Cited

U.S. PATENT DOCUMENTS

| | | |
|---|---|---|
| 2005/0187575 A1 | 8/2005 | Hallbeck et al. |
| 2005/0203564 A1 | 9/2005 | Nobles |
| 2005/0228407 A1 | 10/2005 | Nobles et al. |
| 2005/0261708 A1 | 11/2005 | Pasricha et al. |
| 2005/0261710 A1 | 11/2005 | Sakamoto et al. |
| 2005/0277986 A1 | 12/2005 | Foerster et al. |
| 2006/0052813 A1 | 3/2006 | Nobles |
| 2006/0064113 A1 | 3/2006 | Nakao |
| 2006/0064115 A1 | 3/2006 | Allen et al. |
| 2006/0069397 A1 | 3/2006 | Nobles et al. |
| 2006/0074484 A1 | 4/2006 | Huber |
| 2006/0095052 A1 | 5/2006 | Chambers |
| 2006/0195120 A1 | 8/2006 | Nobles et al. |
| 2006/0248691 A1 | 11/2006 | Rosemann |
| 2006/0265010 A1 | 11/2006 | Paraschac et al. |
| 2006/0282088 A1 | 12/2006 | Ryan |
| 2006/0282094 A1 | 12/2006 | Stokes et al. |
| 2006/0282102 A1 | 12/2006 | Nobles et al. |
| 2006/0287657 A1 | 12/2006 | Bachman |
| 2007/0005079 A1 | 1/2007 | Zarbatany et al. |
| 2007/0010829 A1* | 1/2007 | Nobles ............... A61B 17/0487 606/148 |
| 2007/0043385 A1 | 2/2007 | Nobles et al. |
| 2007/0060930 A1 | 3/2007 | Hamilton et al. |
| 2007/0106310 A1 | 5/2007 | Goldin et al. |
| 2007/0118151 A1 | 5/2007 | Davidson |
| 2007/0142846 A1 | 6/2007 | Catanese, III et al. |
| 2007/0213757 A1 | 9/2007 | Boraiah |
| 2007/0219630 A1 | 9/2007 | Chu |
| 2007/0276413 A1 | 11/2007 | Nobles |
| 2007/0276414 A1 | 11/2007 | Nobles |
| 2008/0033459 A1 | 2/2008 | Shafi et al. |
| 2008/0065145 A1 | 3/2008 | Carpenter |
| 2008/0077162 A1 | 3/2008 | Domingo |
| 2008/0114384 A1 | 5/2008 | Chang et al. |
| 2008/0188873 A1 | 8/2008 | Speziali |
| 2008/0228201 A1 | 9/2008 | Zarbatany |
| 2008/0269786 A1 | 10/2008 | Nobles et al. |
| 2008/0269788 A1 | 10/2008 | Phillips |
| 2009/0036906 A1 | 2/2009 | Stafford |
| 2009/0048615 A1 | 2/2009 | McIntosh |
| 2009/0099410 A1 | 4/2009 | De Marchena |
| 2009/0105729 A1 | 4/2009 | Zentgraf |
| 2009/0105751 A1 | 4/2009 | Zentgraf |
| 2009/0118726 A1 | 5/2009 | Auth et al. |
| 2009/0125042 A1 | 5/2009 | Mouw |
| 2009/0287183 A1 | 11/2009 | Bishop et al. |
| 2009/0299409 A1 | 12/2009 | Coe et al. |
| 2009/0312772 A1 | 12/2009 | Chu |
| 2009/0312783 A1 | 12/2009 | Whayne et al. |
| 2009/0312789 A1 | 12/2009 | Kassab et al. |
| 2010/0016870 A1 | 1/2010 | Campbell |
| 2010/0030242 A1 | 2/2010 | Nobles et al. |
| 2010/0042147 A1 | 2/2010 | Janovsky et al. |
| 2010/0063586 A1 | 3/2010 | Hasenkam et al. |
| 2010/0087838 A1 | 4/2010 | Nobles et al. |
| 2010/0094314 A1 | 4/2010 | Hernlund et al. |
| 2010/0100167 A1 | 4/2010 | Bortlein et al. |
| 2010/0179585 A1 | 7/2010 | Carpenter et al. |
| 2010/0210899 A1 | 8/2010 | Schankereli |
| 2011/0190793 A1 | 8/2011 | Nobles et al. |
| 2011/0202077 A1 | 8/2011 | Chin et al. |
| 2011/0208214 A1* | 8/2011 | Poo ................... A61B 17/0469 606/148 |
| 2011/0224720 A1 | 9/2011 | Kassab et al. |
| 2011/0251627 A1 | 10/2011 | Hamilton et al. |
| 2012/0016384 A1 | 1/2012 | Wilke et al. |
| 2012/0035628 A1 | 2/2012 | Aguirre et al. |
| 2012/0059398 A1 | 3/2012 | Pate et al. |
| 2012/0143222 A1 | 6/2012 | Dravis et al. |
| 2012/0165838 A1 | 6/2012 | Kobylewski et al. |
| 2012/0296373 A1 | 11/2012 | Roorda et al. |
| 2013/0103056 A1 | 4/2013 | Chu |
| 2013/0261645 A1 | 10/2013 | Nobles et al. |
| 2013/0324800 A1 | 12/2013 | Cahill |
| 2014/0309670 A1 | 10/2014 | Bakos et al. |
| 2014/0379006 A1 | 12/2014 | Sutherland et al. |
| 2015/0359531 A1 | 12/2015 | Sauer |
| 2016/0151064 A1 | 6/2016 | Nobles |
| 2017/0035425 A1 | 2/2017 | Fegelman et al. |
| 2017/0049451 A1 | 2/2017 | Hausen |
| 2017/0296168 A1 | 4/2017 | Nobles et al. |
| 2017/0128059 A1 | 5/2017 | Coe et al. |
| 2019/0029672 A1 | 1/2019 | Nobles et al. |
| 2019/0150903 A1 | 5/2019 | Nobles |
| 2019/0239880 A1 | 8/2019 | Nobles |

FOREIGN PATENT DOCUMENTS

| | | |
|---|---|---|
| DE | 29 01 701 | 7/1980 |
| EP | 0 241 038 | 10/1987 |
| EP | 0 544 485 | 6/1993 |
| EP | 0839 550 | 5/1998 |
| EP | 0 894 475 | 2/1999 |
| EP | 1 303 218 | 4/2003 |
| EP | 0 941 698 | 5/2005 |
| EP | 0 983 027 | 12/2005 |
| EP | 1 852 071 | 11/2007 |
| EP | 1 987 779 | 11/2008 |
| EP | 2 572 649 | 3/2013 |
| FR | 2 701 401 | 8/1994 |
| JP | A 9507398 | 7/1997 |
| JP | 09-266910 A | 10/1997 |
| JP | H10-43192 | 2/1998 |
| JP | 2001-524864 | 12/2001 |
| JP | 2003-139113 A2 | 5/2003 |
| JP | 2003-225241 A | 8/2003 |
| JP | 2007-503870 | 3/2007 |
| JP | 2008-514305 | 5/2008 |
| JP | 2008-541857 | 11/2008 |
| JP | 2008-546454 | 12/2008 |
| JP | 2009-261960 | 11/2009 |
| JP | 2010-522625 | 7/2010 |
| JP | 2011-067251 | 4/2011 |
| RU | 2010 125954 | 1/2012 |
| SU | 1560129 A1 | 4/1990 |
| WO | WO 92/05828 | 4/1992 |
| WO | WO 93/01750 | 2/1993 |
| WO | WO 93/07800 | 4/1993 |
| WO | WO 95/12429 | 5/1995 |
| WO | WO 95/17127 | 6/1995 |
| WO | WO 95/25468 | 9/1995 |
| WO | WO 95/25470 | 9/1995 |
| WO | WO 96/03083 | 2/1996 |
| WO | WO 96/29012 | 9/1996 |
| WO | WO 96/40347 | 12/1996 |
| WO | WO 97/03613 | 2/1997 |
| WO | WO 97/47261 | 2/1997 |
| WO | WO 97/07745 | 3/1997 |
| WO | WO 97/12540 | 4/1997 |
| WO | WO 97/20505 | 6/1997 |
| WO | WO 97/24975 | 7/1997 |
| WO | WO 97/27807 | 8/1997 |
| WO | WO 97/40738 | 11/1997 |
| WO | WO 98/12970 | 4/1998 |
| WO | WO 98/52476 | 11/1998 |
| WO | WO 99/40851 | 8/1999 |
| WO | WO 99/42160 | 8/1999 |
| WO | WO 99/45848 | 9/1999 |
| WO | WO 00/002489 | 1/2000 |
| WO | WO 01/001868 | 1/2001 |
| WO | WO 01/95809 | 12/2001 |
| WO | WO 02/024078 | 3/2002 |
| WO | WO 04/012789 | 2/2004 |
| WO | WO 04/096013 | 11/2004 |
| WO | WO 06/127636 | 11/2006 |
| WO | WO 07/001936 | 1/2007 |
| WO | WO 07/016261 | 2/2007 |
| WO | WO 08/121738 | 10/2008 |
| WO | WO 09/081396 | 7/2009 |
| WO | WO 09/137766 | 11/2009 |
| WO | WO 11/094619 | 8/2011 |
| WO | WO 11/137224 | 11/2011 |
| WO | WO 11/156782 | 12/2011 |

(56) References Cited

FOREIGN PATENT DOCUMENTS

| WO | WO 12/012336 | 1/2012 |
|----|--------------|--------|
| WO | WO 12/142338 | 10/2012 |
| WO | WO 13/027209 | 2/2013 |
| WO | WO 13/142487 | 9/2013 |
| WO | WO 13/170081 | 11/2013 |
| WO | WO 15/002815 | 1/2015 |
| WO | WO 15/085145 | 6/2015 |
| WO | WO 17/180092 | 10/2017 |
| WO | WO 19/035095 | 2/2019 |
| WO | WO 19/051379 | 3/2019 |
| WO | WO 19/055433 | 3/2019 |

OTHER PUBLICATIONS

Cardio Medical Solutions, Inc. brochure titled: "Baladi Inverter for Clamp less Surgery"—Undated.

Clinical Evaluation of Arteriovenous Fistulas as an Adjunct to Lower Extremity Arterial Reconstructions, by Herbert Dardick, M.D., in Current Critical Problems in Vascular Surgery, copyright 1989 by Quality Medical Publishing Inc., at p. 383.

Current Therapy in Vascular Surgery, 2nd edition, by Calvin B. Ernst, M.D. and James C. Stanley, M.D., copyright 1991 By B.C. Decker, Inc., at pp. A and 140.

Eskuri, A., The Design of a Minimally Invasive Vascular Suturing Device, Thesis submitted to Rose-Hulman Institute of Technology, Nov. 1999.

Manual of Vascular Surgery, vol. 2, Edwin J. Wylie, Ronald J. Stoney, William K. Ehrenfeld and David J. Effeney (Richard H. Egdahl ed.), copyright 1986 by Springer-Verlag New York Inc., at p. 41.

Nursing the Open-Heart Surgery Patient, By Mary Jo Aspinall, R.N., M.N., copyright 1973 by McGraw Hill, Inc., at pp. 216 and 231.

Operative Arterial Surgery, by P.R. Bell, M.D., and W Barrie, M.D., copyright 1981 by Bell, Barrie, and Leicester Royal Infirmary, printed byJohn Wright &Sons, pp. 16, 17, 104, 105, 112, and 113.

Sinus Venous Type of Atrial Septal Defect with Partial Anomalous Pulmonary Venous Return, by Francis Robicsek, MD., et ai, in Journal of Thoracic and Cardiovascular Surgery, Oct. 1979, vol. 78, No. 4, at pp. 559-562.

Techniques in Vascular Surgery, by Denton A. Cooley, MD. and Don C. Wukasch, MD., copyright 1979 by WB. Saunders Co., at pp. 38,57,86,134,156, and 184.

The problem: Closing wounds in deep areas during laparoscopic operations The solution: REMA Medizintechnik GmbH (no date).

Vascular Access, Principles and Practice, 3rd edition, by Samuel Eric Wilson, MD., copyright 1996, 1988, 1980 by Mosby-Year Book, Inc., pp. 89 and 159.

Vascular and Endovascular Surgery, by Jonathan D. Beard and Peter Gainers, copyright 1998 by W. B. Saunders Co., Ltd, p. 414.

Vascular Surgery, 3rd edition, vol. 1, by Robert B. Rutherford, MD., copyright 1989, 1984, 1976 By W. B.SaundersCo., at pp. 347, 348, 354, 594, 607, 622, 675, 677, 680, 698, 700, 721, 727, 735, and 829.

Vascular Surgery, 4th edition by Robert B. Rutherford, MD., copyright 1995,1989,1976, by W.B. Saunders Co., vol. 1, at pp. 400-404, 661, and A.

Vascular Surgery, 4th edition, by Robert B. Rutherford, MD., copyright 1995, 1989, 1984, 1976 by W. B. Saunders Co., vol. 2, at pp. 1318, 1363, 1426, 1564, and 1580.

Vascular Surgery, by Robert B. Rutherford, M.D. copyright1977 by WB. Saunders Co., at pp. 334 and 817.

International Search Report and Written Opinion, re PCT Application No. PCT/IB2018/056250, dated Dec. 12, 2018.

International Preliminary Report on Patentability, re PCT Application No. PCT/IB2018/056250, dated Feb. 18, 2020.

* cited by examiner

APPARATUS FOR APPLYING A KNOT TO A SUTURE

INCORPORATION BY REFERENCE TO ANY RELATED APPLICATIONS

This application is a continuation of International Patent Application No. PCT/IB2018/056250, filed Aug. 17, 2018, entitled APPARATUS FOR APPLYING A KNOT TO A SUTURE, which claims the benefit of priority to U.S. Provisional Patent Application No. 62/547,717, filed Aug. 18, 2017, entitled METHOD AND APPARATUS FOR APPLYING A KNOT TO A SUTURE, the entirety of which is hereby incorporated by reference herein and should be considered part of this specification.

This application is related to U.S. application Ser. No. 12/057,304, filed Mar. 27, 2008 and entitled "SUTURING DEVICES AND METHODS FOR CLOSING A PATENT FORAMEN OVALE", now U.S. Pat. No. 8,246,636, issued Aug. 21, 2017, and U.S. application Ser. No. 13/489,573, filed Jun. 6, 2012 and entitled "METHOD AND APPARATUS FOR APPLYING A KNOT TO A SUTURE", now U.S. Pat. No. 8,469,975, issued Jun. 25, 2013, which are expressly bodily incorporated in their entirety and are part of this disclosure.

TECHNICAL FIELD

The present disclosure relates to suturing devices and methods. Some embodiments relate to devices and methods for closing incisions in vessels or in organs within a body.

BACKGROUND

Surgeons frequently encounter the need to close incisions, wounds, or otherwise joining tissue portions with a suture. After passing the suture through the tissue portions, the surgeon must tie and cinch the suture to draw the tissue portions together and prevent the tissues from separating. When sutures are tied in a region having restricted access, such as the end of a tissue tract leading to an artery or inside a heart of the patient, the surgeon is presented with special challenges. Sutures can often be difficult to handle, thereby increasing the time that it takes for a surgeon to tie a suture. Accordingly, what is needed is a faster and more effective way to tie and cinch a suture.

SUMMARY

Devices that can apply a knot to a suture have been used to tie and cinch the suture in a region with restricted access. In some embodiments, the knot can comprise a knot body and a plug of the type disclosed in FIGS. 10-18C of U.S. Pat. No. 8,469,975, incorporated by reference herein, with the suture trapped between the knot body and the plug. The plug can be advanced by a pusher rod of the knot placement device into the knot body to secure the suture between the knot body and plug. The suture can then be cut by a rotatable cutting surface of the knot placement device and the knot can be ejected from the device.

The knot placement devices and methods in some embodiments of the present disclosure can improve the ease for the user and/or success of ejecting the knot, cutting the suture portions and/or releasing the cut suture portions. The knot placement device can reduce a force required to cut the suture, which can be particularly advantageous for types of sutures that may stretch under a tension imparted by the rotating cutting surface. A knot placement device can include a first actuator configured for advancing the plug into the knot body. The knot placement device can include a second actuator, separate from a first actuator, to completely eject the formed knot. The second actuator can be reversed in its position to allow the cutting surface to be retracted proximally so as to release suture(s) stuck within the device, for example, between a rotating shaft/tube and an internal component of the device.

According to some embodiments, a knot placement device for applying a knot to a suture can comprise an elongate body having a proximal end and a distal end, the elongate body further having a lumen extending from the proximal end to the distal end; a pusher rod slidably disposed within the elongate body; and a handle coupled to the proximal end of the elongate body. The handle can comprise an elongate outer housing having a longitudinal axis, the pusher rod extending distally from the elongate outer housing and connected to an actuator shaft within the elongate outer housing, a first actuator with at least a portion extending outside the outer housing, wherein activating the first actuator can be configured to advance the pusher rod of the knot placement device distally, a second actuator operably coupled to the actuator shaft, the second actuator configured to be translated to further advance the actuator shaft and push rod distally and to retract the actuator shaft and pusher rod proximally, a knob configured to be rotatable about the longitudinal axis, the outer housing having an aperture configured to allow a user to rotate the knob to cut the suture by rotating a cutting surface of the knot placement device, the knob having a resting position, and a friction mechanism operably coupled to the knob and imparting a force against the knob returning to the resting position when a user rotates the knob about the longitudinal axis in a first direction, wherein the friction mechanism can prevent motion other than in the first direction. Advancing the pusher rod distally can be configured to form a knot by advancing a plug into a knot body positioned within the elongate body to secure the suture therebetween and to eject the knot from the elongate body. Retracting the pusher rod proximally can be configured to release the cut suture.

According to some embodiments of a knot placement device, the friction mechanism can comprise a ratcheting mechanism.

According to some embodiments of a knot placement device, the friction mechanism can comprise a ball detent and the knob comprises a plurality of grooves around a circumference of the knob and substantially along the longitudinal axis.

According to some embodiments of a knot placement device, the friction mechanism can comprise a living hinge and the knob comprises a plurality of grooves around a circumference of the knob and substantially along the longitudinal axis.

According to some embodiments of a knot placement device, the friction mechanism can comprise a leaf spring pressed against the knob.

According to some embodiments of a knot placement device, the friction mechanism can make contact with the knob when the first actuator is advanced into the outer housing.

According to some embodiments of a knot placement device, the friction mechanism can be configured to impart the frictional force against the knob returning to the resting position until the user overcomes the frictional force by further rotating the knob in the first direction.

According to some embodiments of a knot placement device, the knob can remain in place upon release by a user.

According to some embodiments of a knot placement device, the second actuator can comprise at least one tooth configured to mate with at least one rib on the actuator shaft transverse to the longitudinal axis, wherein the mating of the at least one tooth and at least one rib can allow movements of the second actuator to translate to linear movements of the actuator shaft.

According to some embodiments of a knot placement device, the second actuator can comprise a lever arm having a long arm and a short arm divided by a pivot point, wherein the long arm can be configured to rotate proximally to further advance the actuator shaft distally and to rotate distally to retract the actuator shaft proximally.

According to some embodiments of a knot placement device, the long arm can comprise a thumb loop.

According to some embodiments of a knot placement device, the short arm can comprise a plurality of teeth and the actuator shaft can comprise a gear rack, wherein the plurality of teeth can mesh with teeth of the gear rack when the lever arm is rotated about the pivot point.

According to some embodiments of a knot placement device, the gear rack and the knob can comprise a single-piece structure.

According to some embodiments of a knot placement device, the long arm can be at a distalmost position at a start of a knot placement procedure.

According to some embodiments of a knot placement device, the knob can be spring-biased onto the friction mechanism.

According to some embodiments of a knot placement device, the knob can be non-rotatable until the actuator shaft is advanced by deploying the first actuator.

According to some embodiments of a knot placement device, the knob can be coupled to the actuator shaft.

According to some embodiments of a knot placement device, the knob can be generally concentric with the actuator shaft.

According to some embodiments of a knot placement device, an internal wall of the outer housing can comprise a segment of partitions extending generally along the longitudinal axis. The actuator shaft can comprise a pin extending transverse to the longitudinal axis and a space between two adjacent partitions can be configured to accommodate the pin to resist rotation of the actuator shaft and the knob.

According to some embodiments of a knot placement device, the pin can move to be distal of the segment of partitions after deploying the first actuator into a segment of the outer housing having an inner compartment dimensioned to allow rotation of the pin about the longitudinal axis.

According to some embodiments of a knot placement device, the first actuator can comprise a button.

According to some embodiments of a knot placement device, the actuator shaft can be spring-loaded such that advancing the first actuator into the outer housing causes the actuator shaft to spring distally from a retracted position.

According to some embodiments of a knot placement device, the aperture of the outer housing can be dimensioned to allow the user to view the position of the knob throughout use of the handle.

According to some embodiments of a knot placement device, the plug can be positioned proximal of the knot body when undeployed.

According to some embodiments, a method of applying a knot to two or more suture portions can be performed using a knot placement device. The knot can comprise a knot body and a plug configured to secure the suture portions therebetween. The knot placement device can comprise a handle and an elongate shaft extending distally from the handle, The method can comprise advancing a distal portion of the knot placement device to a location near tissue adjacent an opening, wherein the two or more suture portions are positioned within a knot body located in the distal portion, the distal portion further comprising a plug slidably disposed therein proximal to the knot body; actuating a first actuator of the handle to advance the plug toward the knot body to fixedly secure the two or more suture portions between the knot body and an outer surface of the plug by pushing the plug using a pusher rod, the pusher rod operably coupled to the first actuator; actuating a second actuator of the handle to further distally advance the pusher rod to eject the plug and knot body fixedly securing the two or more suture portions from the distal portion of the knot placement device; and rotating in a first direction a rotatable knob about a longitudinal axis of the handle to rotate a cutting surface of the knot placement device to cut the suture portions, wherein the knob can be configured to remain in place upon release by a user.

According to some embodiments of a method of applying a knot to two or more suture portions, translating the second actuator can further comprise advancing the cutting surface distally.

A knot placement device can comprise one or more of the features described in the foregoing description.

A method of applying a knot to a suture can comprise one or more of the features described in the foregoing description.

BRIEF DESCRIPTION OF THE DRAWINGS

Various embodiments are depicted in the accompanying drawings for illustrative purposes, and should in no way be interpreted as limiting the scope of the embodiments. In addition, various features of different disclosed embodiments can be combined to form additional embodiments, which are part of this disclosure.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Overview of Applying a Knot to a Suture in a Location with Restricted Access

Embodiments of the present disclosure relate to applying a knot to two or more suture portions for closing tissue. The two or more suture portions can be portions of the same suture or two or more different suture strands. The two or more suture portions can extend from a treatment location of a patient and can extend outside the patient's body. The treatment location can be any desired location, such as an arterial vessel, a venous vessel, heart tissue, muscle, or any other body tissue, and the particular tissue is not limiting.

Figure 1A:
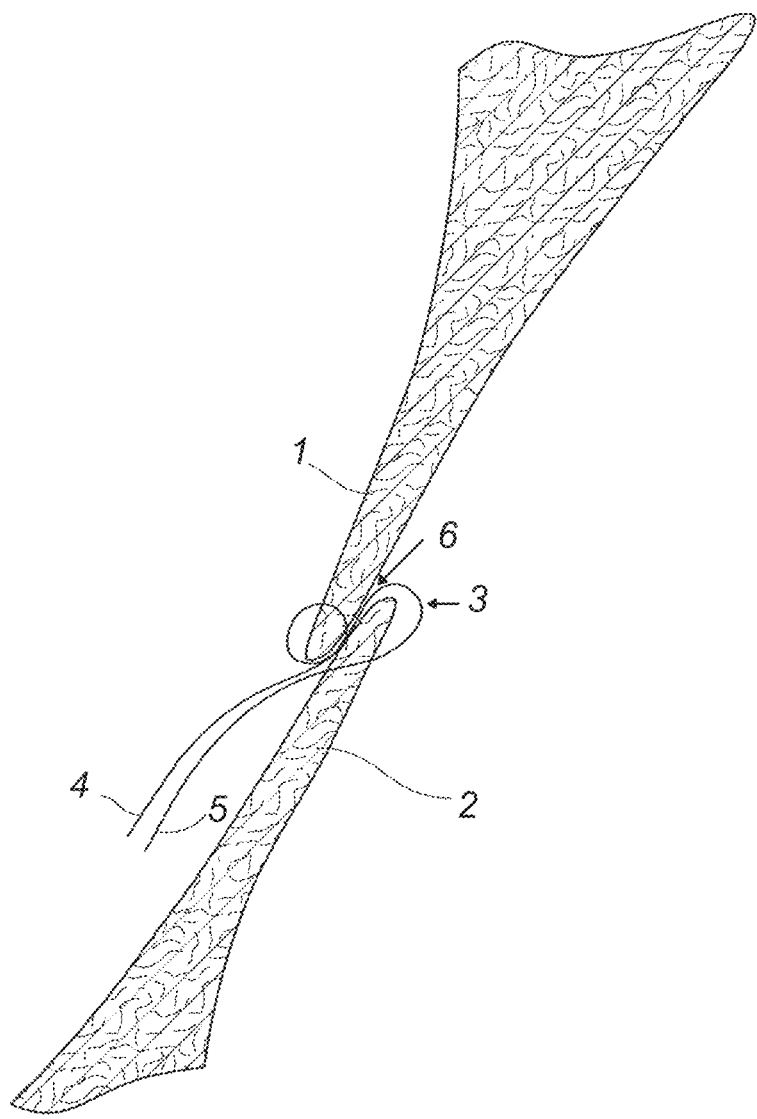
FIG. 1A is a schematic representation of suture portions positioned through a septum secundum and a septum primum following withdrawal of a suturing device deployed in a patent foramen ovale ("PFO").

FIG. 1A illustrates a PFO, which is an example of a treatment location that needs to be closed. This provides an example of closure of a particular type of tissue, but it will be understood that the disclosed device is not limited to only the closure of the PFO, and it can be used for the closure of other tissues as well. The foramen ovale is a specialized channel because most of the fetus' circulation is shunted away from the lungs during development of a fetus in utero. At that stage, blood is generally oxygenated by the mother's placenta, not the fetus' developing lungs. The foramen ovale is a flap-like opening between the atrial septa primum 2 and secundum 1 which serves as a physiologic conduit for right to left shunting between the atria. Typically, once the pulmonary circulation is established in an infant after birth, left atrial pressure increases, resulting in the fusing of the septum primum 2 and septum secundum 1 and thus the closure of the foramen ovale. Occasionally, however, the foramen ovale fails to close and can create hemodynamic problems in the infant, which may be fatal unless treated. A foramen ovale which does not seal after birth is defined as a patent foramen ovale, or PFO, 6.

As shown in FIG. 1A, a suture portion 4 can be positioned through the septum primum 2 while a suture portion 5 can be positioned through the septum secundum 1 by a suturing device, such as any of the devices described in U.S. Pat. No. 8,246,636, incorporated by reference herein. The suture portions 4 and 5 can be two ends of the same suture strand 3. In other embodiments, the suture portions 4 and 5 can be ends of separate suture strands. After the suturing device is withdrawn, the suture portions 4 and 5 can extend from the PFO 6. The suture portions 4 and 5 can be secured together to close the PFO 6. To form a knot within the patient's heart to close the sutures, which has restricted access, the knot can be tied outside the patient's body and passed to the desired location, or be tied using a knot placement device as described herein. Any excess portion of the suture strand 3 can then be trimmed.

Figure 1B:
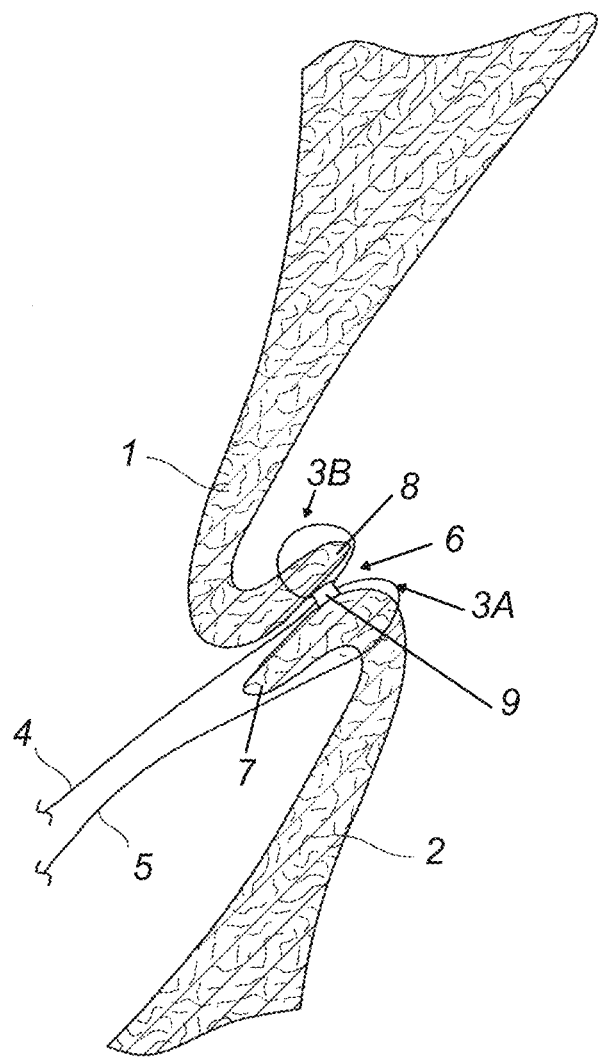
FIG. 1B is another schematic representation of suture portions positioned through a septum secundum and a septum primum following withdrawal of a suturing device deployed in a PFO.

Turning to FIG. 1B, the suture strands 3A, 3B can then be pulled to draw the septum secundum 1 and septum primum 2 towards each other to close the PFO 6. As the suture strands 3A and 3B are pulled tight, the septum secundum 1 and septum primum 2 can be turned or folded so that a tip 7 of the septum primum 2 extends in an opposite direction compared to a tip 8 of the septum secundum 1.

The suture strands 3A, 3B can then be secured together to close the PFO 6. With continued reference to FIG. 1B, a first knot 9 can be positioned between the septum primum 2 and the septum secundum 1. Such placement of the first knot 9 can agitate the tissue and promote healing between the septum primum 2 and the septum secundum 1. The first knot 9 can be positioned between the septum primum 2 and the septum secundum 1 by first tightening the suture strand 3B until the first knot 9 is pulled against the septum secundum 1 then tightening the suture strand 3A to close the PFO 6. Although not illustrated in FIG. 1B, a second knot can be secured between the suture portions 4 and 5.

Knot Placement Device

Figure 2:
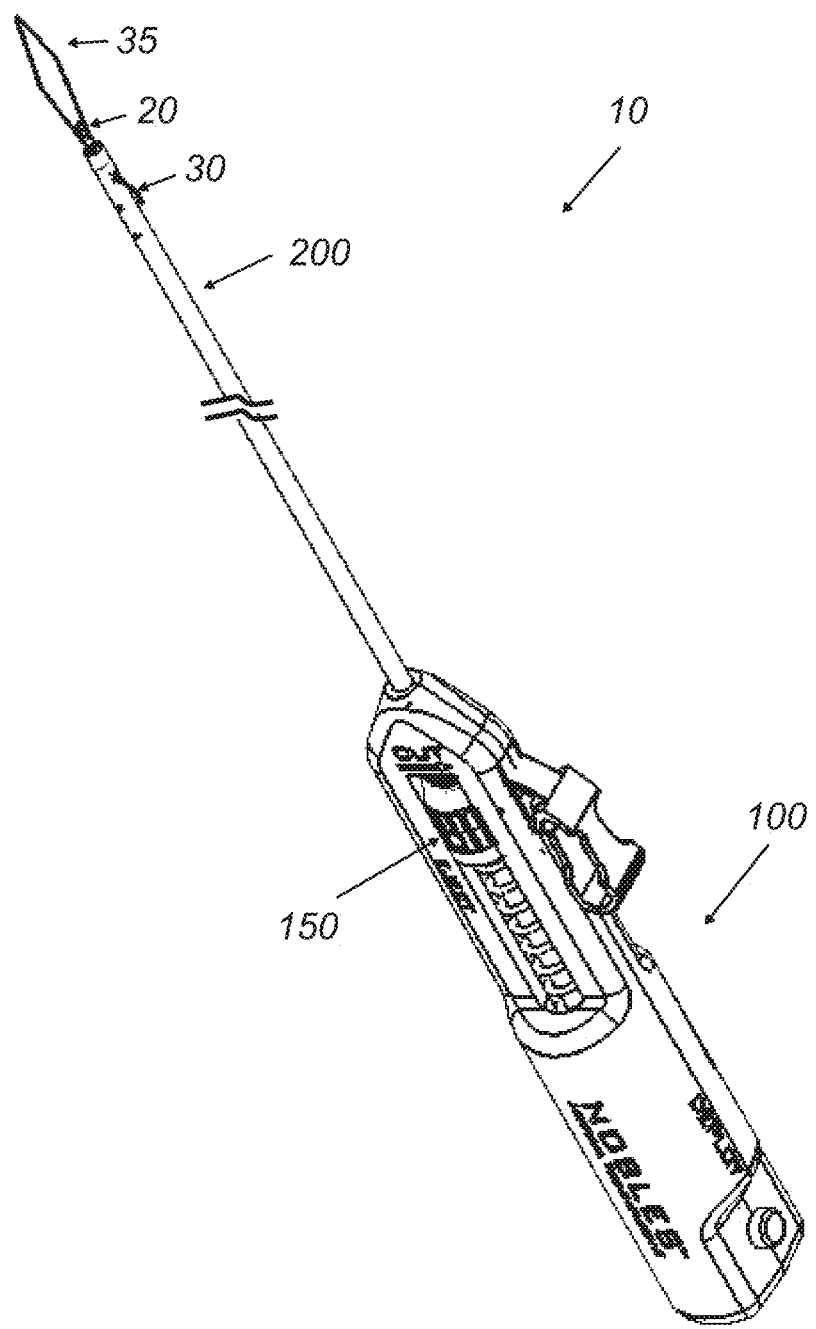
FIG. 2 is a perspective view of an example knot placement device with a partially exploded view of a distal end to show a knot having a knot body and a plug.

Embodiments of knot placement devices described herein can provide a faster and more effective way of tying and cinching a suture, such as to close a PFO or to close an incision/tear in other tissue, or to close any opening, or to bring portions of the same or different tissues closer together. As shown in FIG. 2, the knot placement device 10 can comprise a handle 100 and an elongate member 200 extending distally from the handle 100. A distal portion of the elongate member can contain a knot body and a knot plug (shown in FIG. 12C) forming a knot 20. Two or more suture portions 30 can be secured between the knot body and the plug to form the knot 20. The knot placement device 10 can include a threader 35 configured to load the two or more suture portions 30 into the knot placement device 10. The knot placement devices of the present disclosure can have the same or similar features as the devices described in U.S. Pat. Nos. 8,246,636 and 8,469,975, but can differ in some respects.

Embodiments of the knot placement devices and methods of the present disclosure can improve the ease for the user and/or success of ejecting the knot, cutting the suture portions and/or releasing the cut suture portions. This can allow for an easier "one-handed" approach for a user when manipulating the device.

Specifically, the knot placement device 10 can have a rotatory component 150 on the handle for cutting the suture and can stay in place after a user releases the rotatory component 150. This feature can reduce a force required to cut the suture, in particular, types of sutures that may stretch under a tension imparted by the cutting surface. In some embodiments, the rotatory component 150 can be configured to rotate in only one direction, only clockwise or only counterclockwise.

The knot placement device 10 can include a first actuator 120, which can be configured to advance the plug from a retracted position into the knot body. The first actuator 120 can also ejected the knot from the knot placement device 10. The knot placement device 10 can also include a second actuator 130 to completely eject the formed knot. The second actuator 130 can be separate from the first actuator 120. Further, the second actuator 130 can be reversed in its position to retract proximally a pusher rod and a cutting surface (shown in FIG. 12C) of the knot placement device 10. Reversing the position of the second actuator 130 can to release suture portions(s) stuck within the device, for example, between a rotating shaft/tube and an internal component of the device 10.

Handle of a Knot Placement Device

Figure 3A:
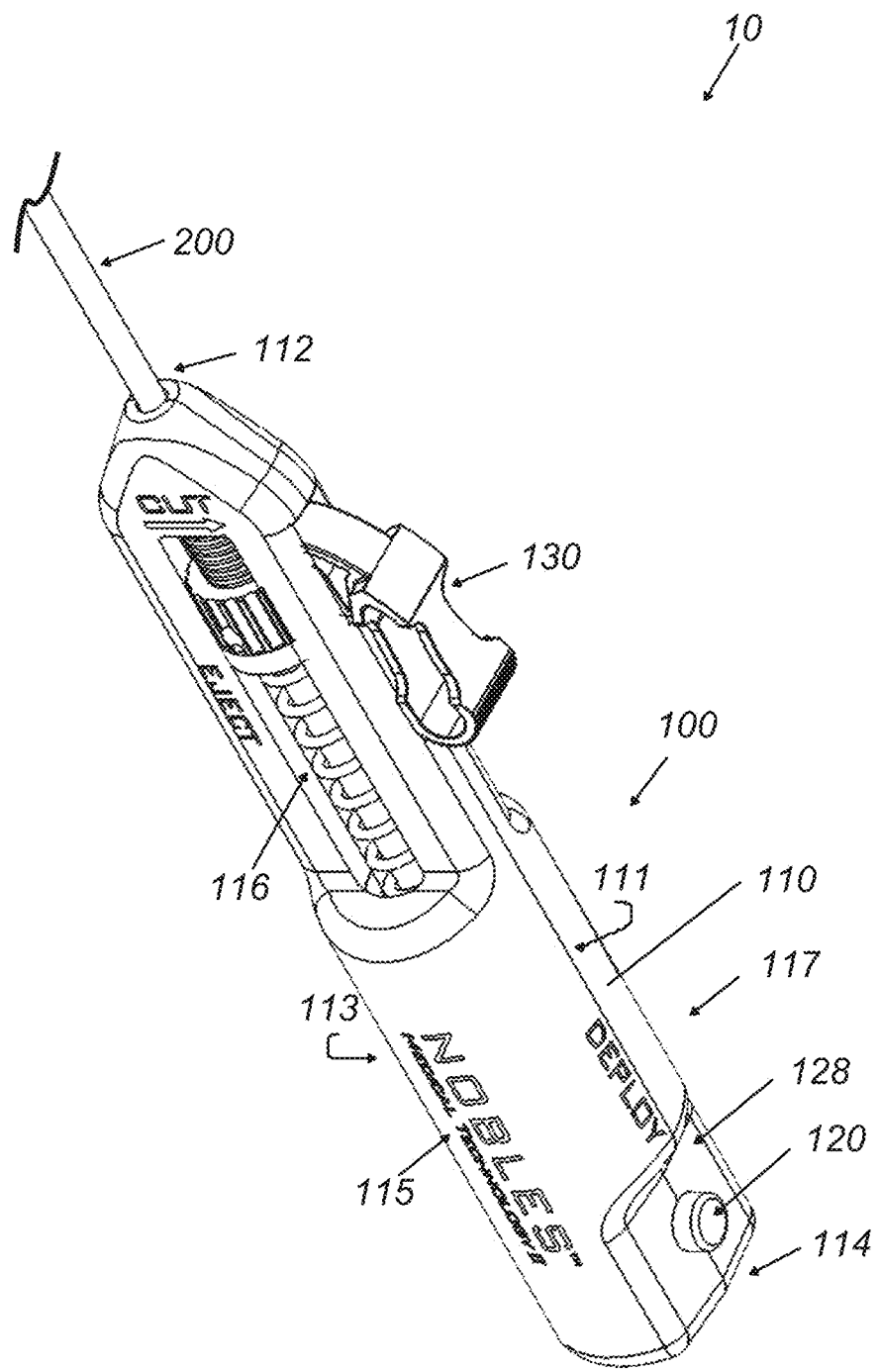
FIGS. 3A-3B are perspective and side views of an example handle of a knot placement device.
Figure 3B:
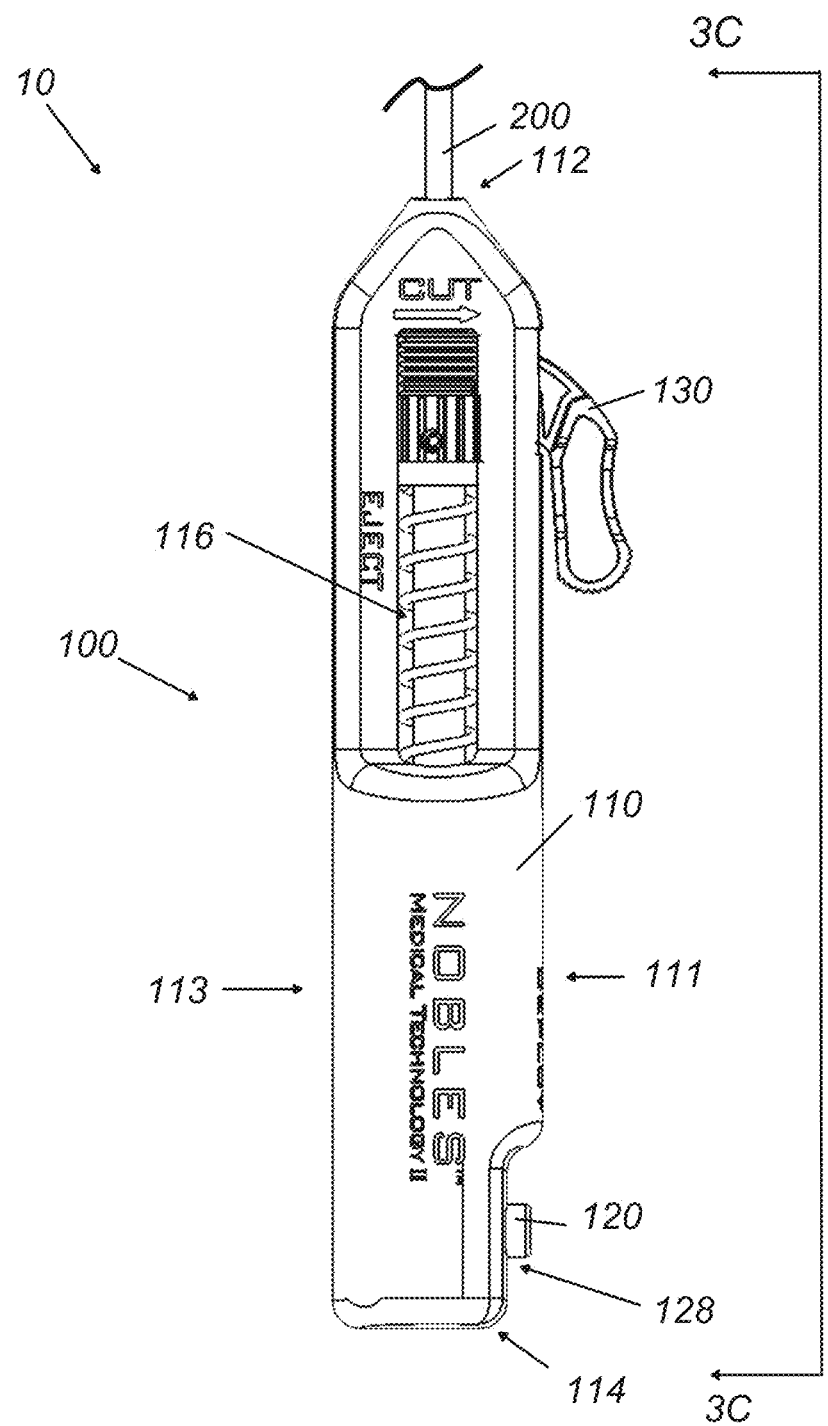

Turning to FIGS. 3A and 3B, an embodiment of the knot placement device 10 can have a handle 100 coupled to an elongate member 200 extending distally from the handle 100 for placing the knot at a target treatment location. Preferably, the elongate member 200 can be flexible. The handle 100 can comprise an outer housing 110 having an elongate body defining a longitudinal axis and configured for being held by a user's hand. In some embodiments, the outer housing 110 can comprise two half housings attached to one another, such as through mechanical forces or adhesive forces. The two half housings can be mirror images of each other, though in some embodiments there can be variations of the housing.

The outer housing 110 can have a distal end 112 and a proximal end 114, which can define distal and proximal ends of the handle 100. The outer housing 110 can also have an upper side 111 and a lower side 113, and a left side 115 and a right side 117. The distal end 112 of the outer housing 110 can have an opening dimensioned to accommodate a proximal portion of the elongate member 200.

The proximal end 114 of the outer housing 110 can be a closed end and can have the first actuator 120 close to the proximal end 114. In some embodiments, the first actuator 120 can be located elsewhere on the outer housing 110. The first actuator 120 can be a button as shown in FIG. 3A, or another actuator such as a switch, lever, etc.

The outer housing 110 can comprise a slot on the upper side 111 for accommodating the second actuator 130. As illustrated in the figures in the present disclosure, the slot can be formed near the distal end 112 of the outer housing 110. In some embodiments, the second actuator 130 can be located on the same side of the outer housing 110 as the first actuator 120. In other embodiments, the slot can be located more proximally, and/or can be located on the lower side 113, or anywhere on the left or right sides 115, 117.

The outer housing 110 can have an aperture 116 generally along the longitudinal axis. The aperture 116 can have a generally rectangular or oval shape, although the shape of the aperture 116 is not limiting. The aperture 116 can be formed on the left side 115, or the right side 117, or both. A person of ordinary skill in the art will recognize from the disclosure herein that the aperture 116 can be formed on other side(s) of the outer housing 110. As will be described in greater detail below, the aperture 116 can provide viewing by the user of positions of certain components that are at least partially enclosed within the outer housing 110, and/or allow manipulation by the user of one or more of those components.

Figure 3C:
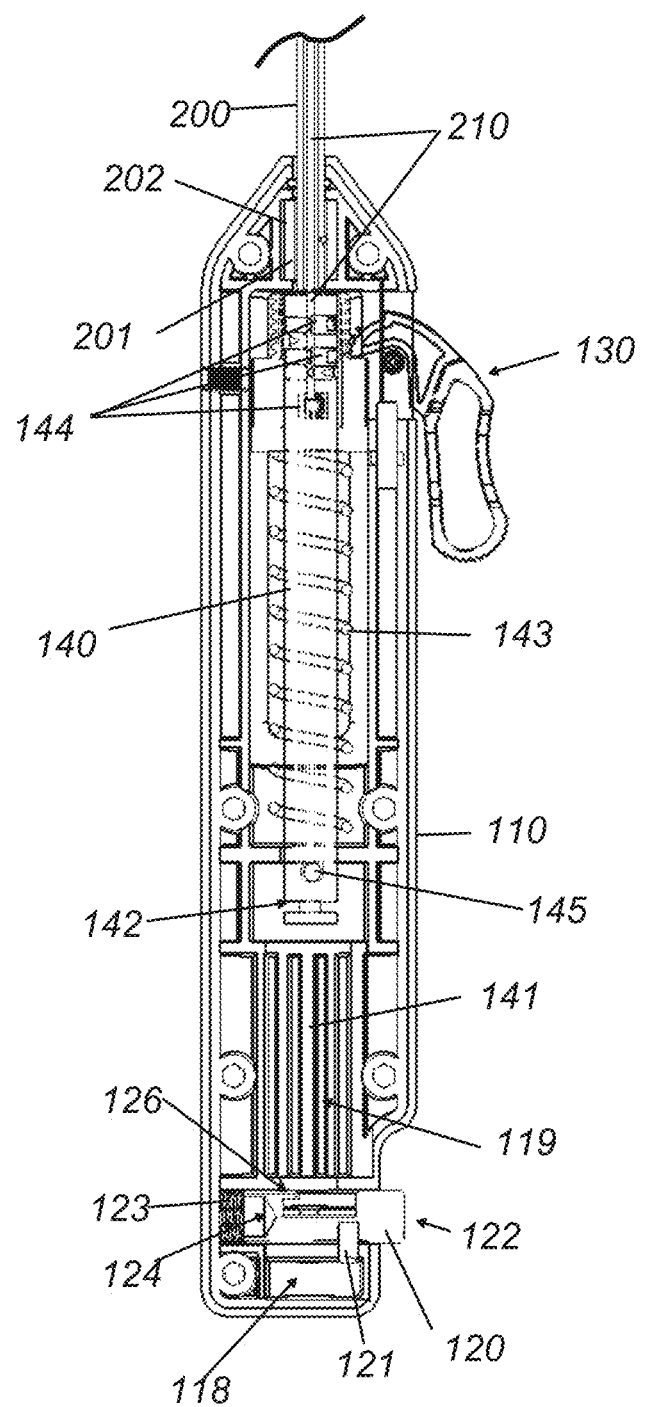
FIG. 3C is a cross-sectional view of the handle of FIG. 3B taken along the line 3C-3C.

Turning to FIG. 3C, the outer housing 110 can enclose an actuator shaft 140. The actuator shaft 140 can have an elongate body running generally parallel to the longitudinal axis of the outer housing 110. As shown in FIG. 3C, the proximal portion of the elongate member 200 can extend proximally into a mounting recess 201 of the outer housing 110 of the handle 100 via the opening at its distal end 112. The mounting recess 201 can accommodate, support, and limit movements of a mounting hub 202. The mounting hub 202 can be fixedly attached to the proximal portion of the elongate member 200. The proximal portion of the elongate member 200 can terminate at or close to a distal end surface of the actuator shaft 140. The proximal portion of the elongate member 200 can be decoupled from the actuator shaft 140. The elongate member 200 can have a through-lumen and can house a pusher rod 210 slidably disposed within the elongate member 200. A proximal portion of the pusher rod 210 can extend proximally into the outer housing 110 and also into a portion of the actuator shaft 140. The proximal portion of the pusher rod 210 can be fixedly coupled to the actuator shaft 140, for example, with a plurality of set screws 144 in a plurality of directions transverse to the longitudinal axis. A plurality of positioning pins can also be used to support or fix the pusher rod 210. In some embodiments, the actuator shaft 140 is substantially coaxial with the pusher rod 210 and/or the proximal portion of the elongate member 200.

Figure 8A:
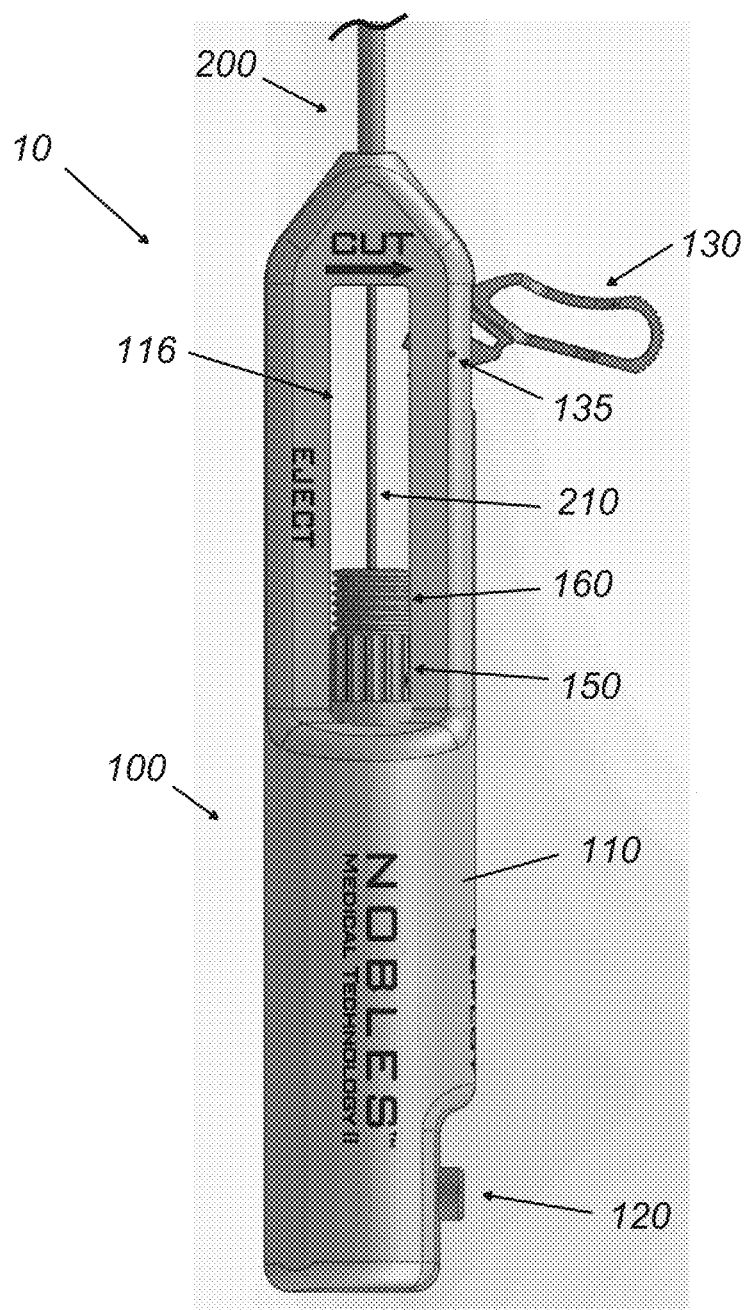
FIG. 8A is a side view of an example handle of a knot placement device at a start of a knot placement procedure.

With continued reference to FIG. 3C, the actuator shaft 140 can be configured to translate proximally and distally along the longitudinal axis of the outer housing 110. The outer housing 110 can have one or more internal partitions and/or guide rails, such as a neck or ring, to guide the linear translation of the actuator shaft 140. FIG. 3C illustrates the actuator shaft 140 when it has been moved to its distalmost position. When at the distalmost position, the actuator shaft 140 can be stopped by an internal transverse wall of the outer housing 110. The actuator shaft 140 can be at its proximalmost position (such as shown in FIG. 8A) at a start of a knot placement procedure.

As shown in FIG. 3C, the actuator shaft 140 can include a recess or groove 142 at its proximal end. When at the proximalmost position, the recess or groove 142 can be configured to engage the first actuator 120, which can hold the actuator shaft 140 in its proximalmost position. Specifically, the first actuator 120 can have a generally cylindrical shape, although the overall shape of the first actuator 120 is not limiting (e.g. a rod with a rectangular, oval, or polygonal cross-section). The first actuator 120 can have an upper end 122 and a lower end 124, and an elongate body between the upper and lower ends 122, 124. The first actuator 120 can be positioned in an opening near the proximal end 114 of the outer housing 110. The opening can extend from the upper side 111 of the outer housing 110 generally toward the lower side 113. A skilled artisan will recognize from the disclosure herein that the opening can also be located on the lower side 113, or the left or right side 115, 117 of the outer housing 110. The opening can open into an internal compartment 118 near the proximal end 114 of the outer housing 110. The first actuator 120 can be positioned into the internal compartment 118 through the opening with the lower end 124 facing the lower side 113 and the elongate body generally transverse to the longitudinal axis of the outer housing 110.

With continued reference to FIG. 3C, a first spring 123 can be positioned underneath the lower end 124 of the first actuator 120. The first spring 123 can bias the first actuator 120 such that the upper end 122 of the first actuator 120 protrudes outside the outer housing 110. As shown in FIGS. 3A and 3B, the first actuator 120 can have an appearance of a button. The outer housing 110 can include a recessed portion 128 for accommodating the portion of the first actuator 120 that protrudes outside the outer housing 110. The recessed portion 128 can reduce the likelihood of a user's hand inadvertently and/or prematurely pressing on the first actuator 120 when the user holds the handle 100 in hand. Returning to FIG. 3C, the first actuator 120 can have a hole near its upper end 122 generally parallel to the longitudinal axis of the outer housing 110 when the first actuator 120 is positioned at least partially within the internal compartment 118. A stopper pin 121 can be inserted partially into the hole. When the first actuator 120 is positioned within the internal compartment 118, a portion of the stopper pin 121 protruding from the first actuator 120 can abut against a wall of the internal compartment 118, such as an upper wall. The stopper pin 121 can thus resist the biasing force of the spring 124 and prevent the first actuator 120 from being completely forced out of the internal compartment 118. As further shown in FIG. 3C, the first actuator 120 can include a hook or projection 126 extending generally transverse to the longitudinal axis of the outer housing 110. The hook or projection 126 can engage the recess 142 on the actuator shaft 140 to retain the actuator shaft 140 in the proximalmost position. A user can advance the first actuator 120 in the outer housing 110, for example, by applying a force on the upper end 122 of the first actuator toward the lower side 113 of the outer housing 110. The force can overcome the biasing force of the first spring 123 and can move the hook or projection 126 out of engagement with the recess 142 of the actuator shaft 140.

As further shown in FIG. 3C, the actuator shaft 140 can be at least partially surrounded by a second spring 143. When the recess 142 of the actuator shaft 140 is released from the hook or projection 126 of the first actuator 120, the second spring 143 can bias the actuator shaft 140 distally. In some embodiments, the actuator shaft 140 can be sprung distally until a drum or knob 150 engages a friction surface 155, and/or a gear rack 160 engages a plurality of teeth 165 of the second actuator 130, which will now be described with reference to FIGS. 4A-7.

Figure 4A:
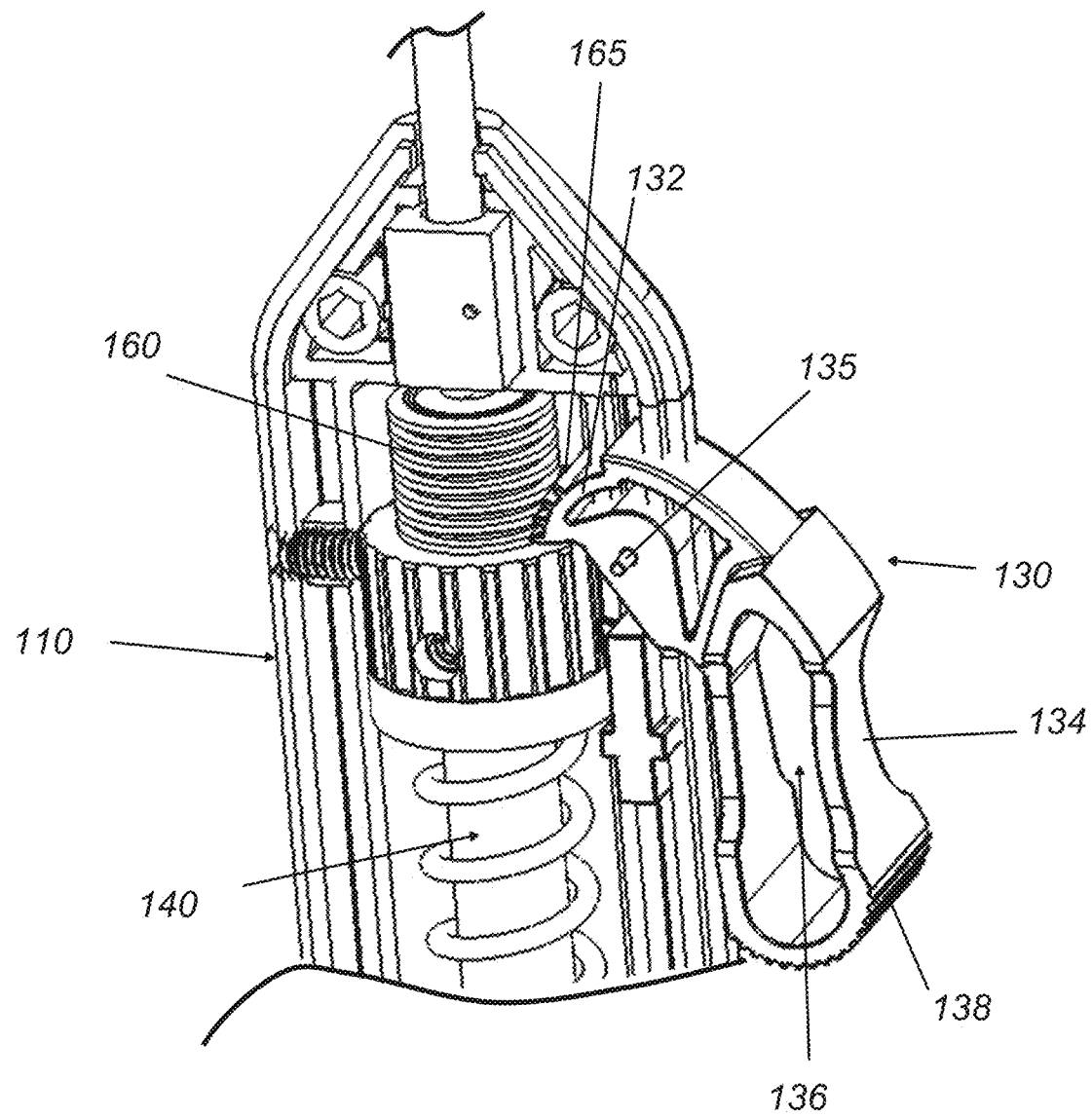
FIG. 4A is a detailed perspective view of a distal portion of the handle of FIG. 3A with half of a handle housing hidden for clarity.

As shown in FIG. 4A, the gear rack 160 can have a generally cylindrical shape and mounted substantially parallel to the longitudinal axis of the outer housing 110. The gear rack 160 can have a plurality of gear teeth (e.g., threads, protrusions) arranged generally parallel to the longitudinal axis of the outer housing 110. The gear rack 160 can be generally concentrically disposed outside a distal portion of the actuator shaft 140. The gear rack 160 can be operably coupled to the actuator shaft 140, such as by an interference fit or fasteners (e.g. set screws mounted radially) or chemicals (such as adhesives) holding the gear rack 160 and the actuator shaft 140 together. Linear and/or rotational movements of the gear rack 160 can be translated to the actuator shaft 140.

With continued reference to FIG. 4A, the second actuator 130 can have a general shape of a lever arm pivoted at a pivot pin 135. The pivot pin 132 can be fixedly inserted into one or two holes on the outer housing 110 and can slide through a pin hole on the second actuator 130. In some embodiments, the pivot pin 132 can be an interference-fit pin (e.g. as shown in FIG. 8A) that is inserted, during assembly, from outside the outer housing 110 on one side (such as the left side 115) into the outer housing 110 and through the pin hole of the second actuator 130, and optionally into an opposite side (such as the right side 117) of the outer housing 110. The tolerances of the pin hole of the second actuator 130 and the pivot pin 135 can be configured to allow the second actuator 130 to rotate unhindered or easily about the pivot pin 135 without being wobbly around the pivot pin 135.

Figure 4B:
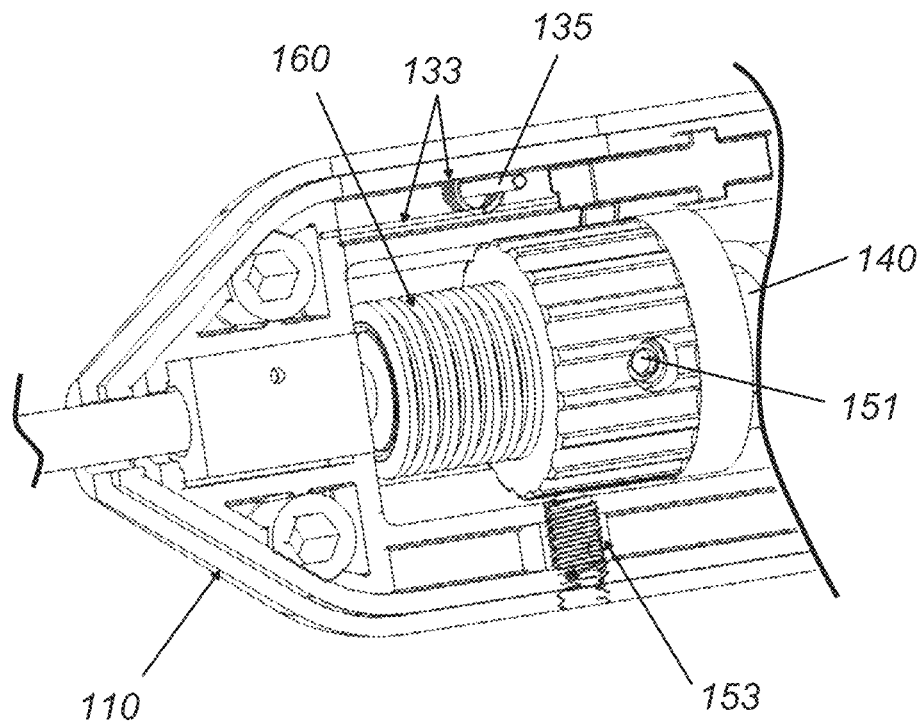
FIG. 4B is a detailed perspective view of the distal portion of the handle of FIG. 3A with half of a handle housing and an actuator hidden for clarity.
Figure 4C:
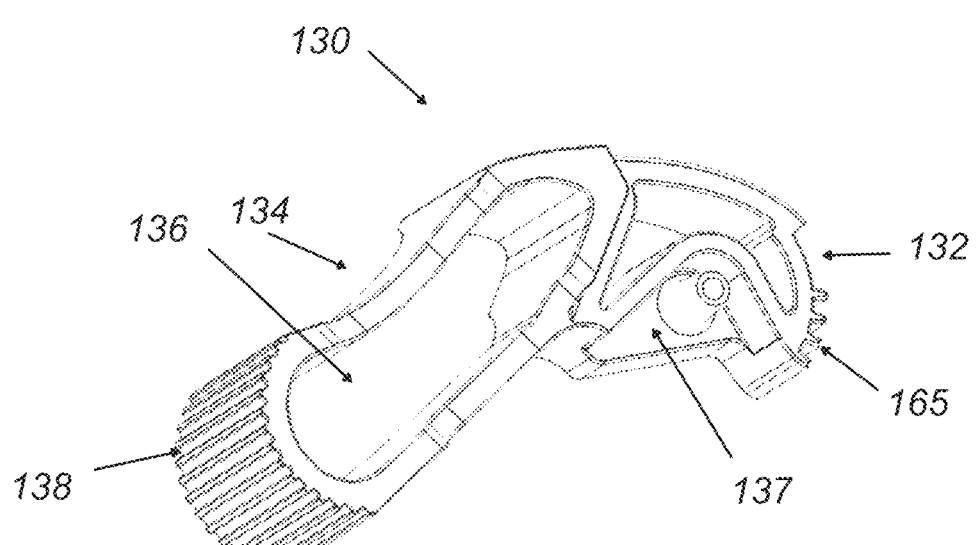
FIG. 4C is a perspective view of an example actuator.

As shown in FIGS. 4A and 4C, the second actuator 130 can have a short arm 132 on one side of the pin hole and within the outer housing 110 and a long arm 134 on a generally opposite side of the pin hole and extending away from the outer housing 110. The short arm 132 can comprise a plurality of teeth 165. The plurality of teeth 165 can be distributed along a curved portion of the short arm 132 so as to form a partial-pinion. The plurality of teeth 165 can be configured to mesh with the teeth in the gear rack 160. Thus, the engagements of the plurality of teeth 165 on the partial-pinion and the plurality of gear teeth on the gear rack 160 can convert a rotatory movement of the second actuator 130 about the pivot pin 135 to a linear movement of the gear rack 160, and thus the actuator shaft 140.

The long arm 134 can have a length that is a few times greater than a length of the short arm 132. When rotating the second actuator 130 about the pivot pin 135, a force imparted on a free end of the long arm 134 can be amplified at or around a free end of the short arm 132 including the plurality of teeth 165, making it easier or less force-intensive for a user to move linearly the gear rack 160 and the actuator shaft 140, and in turn the pusher rod 210 (FIG. 3C). For example, the force required to rotate the long arm 134 of the second actuator 130 can be sufficiently low so that the user is able to rotate the long arm 134 of the second actuator 130 in a single-hand maneuver. In some embodiments, the free end of the long arm 134 can include a thumb loop 136 configured to fit a thumb or any finger of the user. The free end of the long arm 134 can include a rough, knurled, or ribbed outer surface 138, in addition and/or alternative to the thumb loop 136. The thumb loop 136 and/or the rough outer surface 138 can provide greater traction between the user's finger and the second actuator 130, and can further allow easier manipulation, such as a single-handed manipulation of the second actuator 130 by the user.

Turning to FIG. 4B, a torsional spring 133 can be installed generally about the pivot pin 135 between the second actuator 130 and an inner wall of the outer housing 110. The torsional spring 133 can be at least partially disposed in a recess 137 (FIG. 4C) of the second actuator 130. The torsional spring 133 can bias the long arm 134 of the second actuator 130 at a distalmost position and the plurality of teeth 165 at a proximalmost position. The gear rack 160 and the actuator shaft 140 can be proximal of and detached from the plurality of teeth 165 when the long arm 134 of the second actuator 130 is at the proximalmost position. For example, the gear rack 160 and the actuator shaft 140 can be at their proximalmost, or retracted, position. The user can view the position of the gear rack 160 and optionally a portion of the actuator shaft 140 via the aperture 116 of the outer housing 110 throughout the use of the knot placement device 10.

Figure 11:
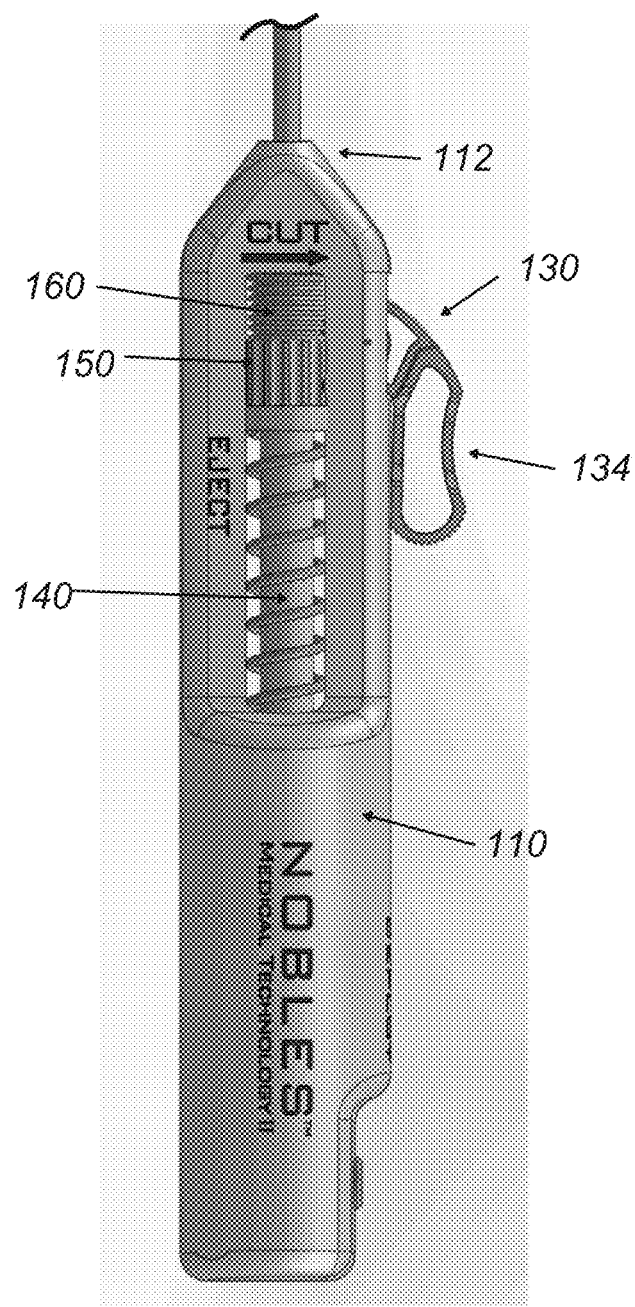
FIG. 11 is a side view of the handle of FIG. 8A when the lever arm is rotated to a proximalmost position.

The aperture 116 can allow the user to have a visual confirmation of distal advancements of the gear rack 160 and the actuator shaft 140 during a knot placement procedure. The visual confirmation from the aperture 116 and/or the increasingly proximal position of the long arm 134 of the second actuator 130 can provide an indication to the user that the plug is being advanced into the knot body to form the knot, and/or that the formed knot is being ejected from the knot placement device. The aperture 116 can allow the user to have additional visual confirmation that the gear rack 160 and the actuator shaft 140 are at the distalmost or fully deployed position, corresponding to when the long arm 134 of the second actuator 130 is rotated to its proximalmost position (such as shown in FIG. 11). This can indicate that the knot has been properly formed and has been ejected from the distal portion of the knot placement device 10. In some embodiments, a maximal linear travel distance of the gear rack 160 and the actuator shaft 140 within the outer housing 110 can be substantially the same or slightly greater than a distance between a distal end of the pusher rod 210 and a distal end of the elongate member. The visual confirmations of the positions of the gear rack 160 and the actuator shaft 140, and optionally also the relative positions of the long arm 134 of the second actuator 130, can be helpful to the user. This is because it can be difficult and inconvenient, if not impossible, for the user to have direct visual confirmations of the formation and ejection of the knot inside the patient, for example, inside the patient's heart. Having separate indications of the formation of the knot and the ejection of the formed knot can provide additional assurance to the user that the knot has been properly formed and ejected from the knot placement device 10.

In some embodiments, the long arm 134 of the second actuator 130 can be moved to its proximalmost position by a distal force upon deploying the first actuator 120. For example, the second spring 143 can provide sufficient biasing force to push the actuator shaft 140 distally until the gear rack 160 contacts an inner transverse wall of the outer housing 110. Manual proximal movement of the long arm 134 to further distally advance the pusher rod 210 can be an optional step performed by the user when deploying or pressing the first actuator 120 does not advance the pusher rod 210 sufficiently to properly form and/or eject the knot. The long arm 134 can still be moved distally by the user to retract the pusher rod 210 to dislodge the cut suture portions.

A skilled artisan will recognize from the description herein that alternative to the gear rack and partial pinion design described above, the second actuator 130 can include a slider configured to operably and releasably engage the actuator shaft 140, for example, with a ball detent and groove arrangement. The slider can translate distally to move the actuator shaft 140 distally and translate proximally to move the actuator shaft 140 proximally. Other forms of linear motion mechanisms can be used to further advance the actuator shaft 140, and in turn the pusher rod 210, in a proximal-to-distal direction, such as a worm drive comprising a worm that meshes with the gear rack 160.

Figure 5:
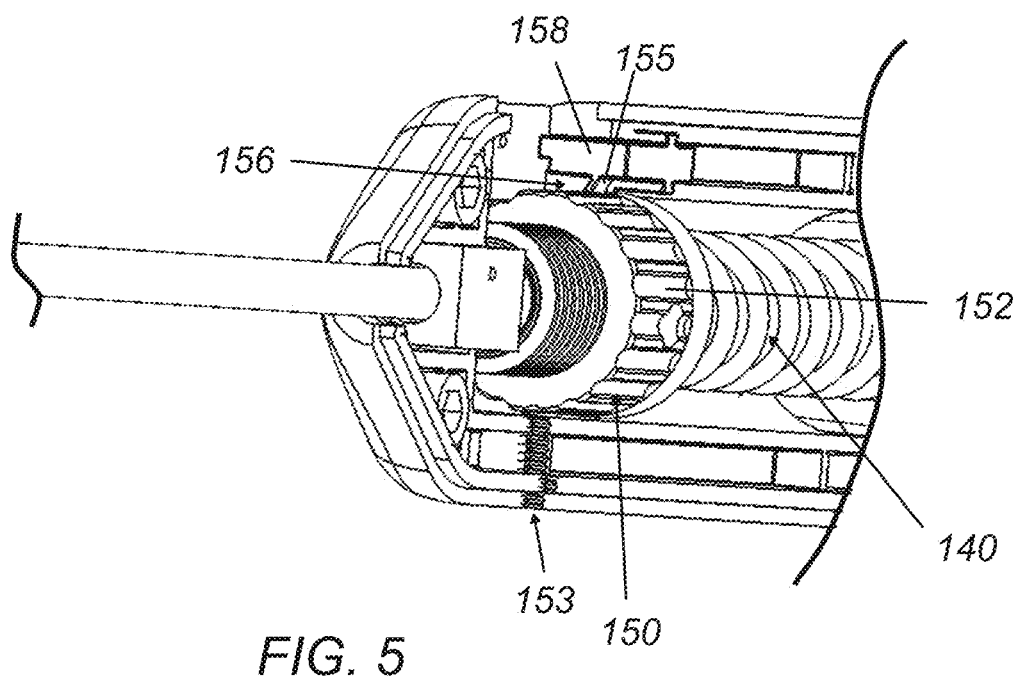
FIG. 5 is a detailed perspective view of the distal portion of the handle of FIG. 3A with half of a handle housing, an actuator and associated pivot pin and torsional spring hidden for clarity.
Figure 7:
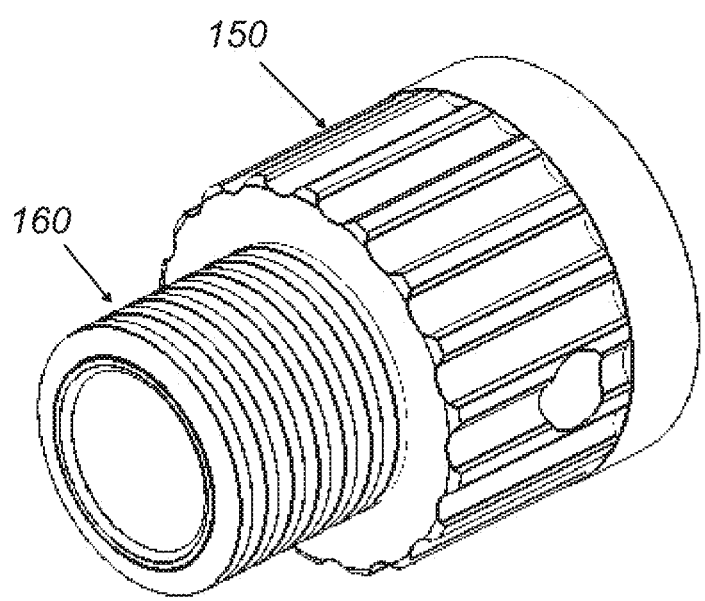
FIG. 7 is a perspective view of a track gear and rotatable knob component.

Turning to FIG. 5, the handle 100 can include a rotatable drum or knob 150. The rotatable drum or knob 150 can rotate about the longitudinal axis of the outer housing 110. The rotatable drum or knob 150 can be operably coupled to the actuator shaft 140, such as by an interference fit or fasteners (e.g., at least one set screw 151 (FIG. 4B) mounted radially) or chemical means (e.g., adhesives) holding the rotatable drum or knob 150 and the actuator shaft 140 together. Linear and/or rotational movements of the rotatable drum or knob 150 can be translated to the actuator shaft 140, and thus the push rod 210. The rotatable drum or knob 150 can be accessed, at least partially, by the user via the aperture 116 of the outer housing 110. The access can be sufficient to allow the user to rotate the drum or knob 150. In some embodiments, the rotation of the drum or knob 150 can be performed single-handedly by the user to free one hand of the user, for example, to manipulate the suture portions. The drum or knob 150 can be bigger than the gear rack 160. The drum or knob 150 can be located proximal to the gear rack 160. These arrangements can reduce the likelihood that the user's hand inadvertently touches or moves the gear rack 160 when rotating the drum or knob 150. In some embodiments, the gear rack 160 and the rotatable drum or knob 150 can be separate components and separately coupled to the actuator shaft 140. As shown in FIG. 7, the gear rack 160 and the rotatable drum or knob 150 can form one single component. The set screw 151 can be configured to fixedly couple both the gear rack 160 and the rotatable drum or knob 150 with the actuator shaft 140. This can reduce the number of fasteners and the number of parts needed to assemble the handle 10, which can simplify the design of the handle 100.

As further shown in FIGS. 5 and 7, the rotatable drum or knob 150 can have a plurality of alternating ridges, teeth, and/or and troughs 152 on an outer surface of the drum or knob 150. The plurality of alternating ridges and troughs 152 can be distributed around a circumference of the drum or knob 150 and can be generally parallel to the longitudinal axis of the outer housing 110. The handle 100 can include a corresponding friction surface 155 that can overlap with a portion of one of the troughs 152 as the drum or knob 150 is rotated. The friction surface 155 can be biased into one of the troughs 152. The biasing can be caused by placing the friction surface 155 at a location so that there is no gap between the friction surface 155 and a surface of one of the troughs 152 of the drum or knob 150. As shown in FIG. 5, the biasing can also be caused in part by a third spring 153, which can push the drum or knob 150 toward the friction surface 155.

Figure 6:
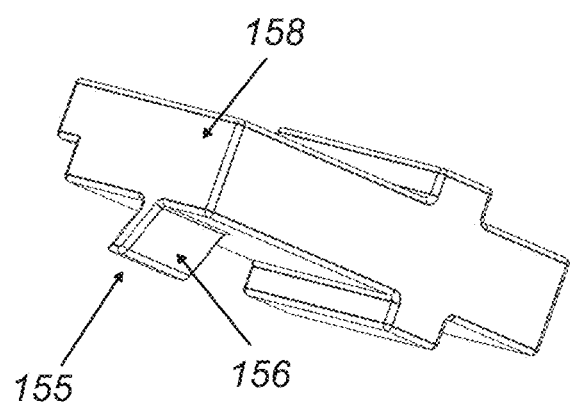
FIG. 6 is a perspective view of an example living hinge component.

As illustrated in FIG. 5 and FIG. 6, the friction surface 155 can be a free end surface of a living hinge flap 156. The living hinge flap 156 can be a thin flap connected to a block 158 forming a monolithic structure. The living hinge flap 156 can bend slightly when it is pressed against a crest of the drum or knob 150 to allow the crest to pass through the living hinge flap 156. The crest may not contact the friction surface 155. In some embodiments, the living hinge flap 156 can be connected to the block 158 at an acute angle, such as shown in FIG. 6, so that the flap 156 can bend slightly when the drum or knob 150 is rotated in a first direction, for example, clockwise when viewed from the proximal side 114 of the outer housing, to allow a crest of the drum or knob 150 to pass. However, the living hinge flap 156 can resist rotation of the drum or knob 150 in an opposite, second direction, for example, counterclockwise when viewed from the proximal side 114 of the outer housing. This can be due to insufficient clearance for the living hinge flap 156 to bend in the opposite direction to allow a crest of the drum or knob 150 to pass.

As a result, the living hinge flap 156 can maintain the drum or knob 150 in place after the user has rotated the drum or knob 150, but releases the drum or knob 150 before having rotated the drum or knob 150 to the fullest extent in the first direction. The user can further rotate the drum or knob 150 in the first direction by applying a rotation force on the drum or knob 150 to overcome the friction between the friction surface 155 and a trough surface of the drum or knob 150. The living hinge feature can make it easier for the user to cut the suture portions and increase the success rate of suture cutting after the knot has been formed. The user does not have to complete rotating the drum or knob 150 in a single maneuver, but can carry out the suture-cutting step in a series of successive incremental rotatory movements. Thus, the user can remove the finger from the drum or knob 150, and the drum or knob 150 will remain in the same position, and not rotate backwards. This can also increase the success rate of cutting sutures made of stretchable materials, such as polypropylene, which may be stretched and resist the cutting force when the drum or knob 150 is not rotated to the fullest extent before reverse the direction of its rotation. This can reduce the force required to rotate the drum or knob 150 and to reduce an overall effort by the user to cut the suture.

A skilled artisan will recognize from the description herein that other one-way friction mechanisms can be used to maintain the drum or knob 150 in place upon release by the user. For example, a ball detent or other types of detent mechanism can replace the living hinge flap 156. The ball detent can engage one of the troughs of the drum or knob 150 when the drum or knob 150 is rotated. In other embodiments, the plurality of ridges and troughs on the drum or knob 150 can have angled teeth to form a ratcheting mechanism with a bar or a pin extending from a stationary location inside the outer housing 110. In other embodiments, the friction surface can be a leaf spring pressed against a smooth-surfaced drum or knob 150 or the drum or knob 150 as shown in the figures in the present disclosure.

Returning to FIG. 3C, the outer housing 110 can be configured to resist rotation of the drum or knob 150 when the drum or knob 150 and the actuator shaft 140 are at their proximalmost position. Correspondingly, a portion of the actuator shaft 140 can be positioned in a compartment 119 in the outer housing 110. There can be a neck or ring within the compartment 119 sized to slidably and rotatably support the actuator shaft 140. Specifically, the compartment 119 can have a plurality of partition walls 141. Free ends of the plurality of partition walls 141 can define the neck or ring. The actuator shaft 140 can include an anti-rotation pin 145, which can be a dowel pin and can at least partially extend or protrude from an outer surface of the actuator shaft 140. The anti-rotation pin 145 can be located distal of the recess 142 on the actuator shaft 140 such that the anti-rotation pin 145 can be between the plurality of partition walls 141 when the actuator shaft 140 is in the proximalmost, or retracted position. The anti-rotation pin 145 can be restricted in rotational movements about the longitudinal axis of the outer housing 110, thus resisting rotation of the actuator shaft 140, and in turn the drum or knob 150. In some embodiments, the anti-rotation pin 145 can be moved sufficiently proximally to clear the compartment 119 and the plurality of partition walls 141 upon deploying the first actuator 120. The anti-rotation pin 145 can then be in a compartment with sufficient clearance for rotating the anti-rotation pin 145 about the longitudinal axis of the outer housing 110, thus allowing the drum or knob 150 to become rotatable. An advantage of preventing the drum or knob 150 from being rotatable before the actuator shaft 140 is advanced distally by deploying the first actuator 120 can be a reduced risk of premature cutting of the suture before a knot has been formed or completely formed. A partially formed knot may not have enough cinching of the suture to sufficiently seal the opening in the tissue. Once the knot has been formed, it can be the user's preference whether to eject the knot before cutting the suture or cutting the suture before ejecting the formed knot.

Method of Apply a Knot to a Suture Using the Knot Placement Device

Example methods of using the knot placement device 10 will now be described with reference to FIGS. 8A to 14B. FIG. 8A illustrates the handle 100 of the knot placement device 10 that is ready for being used to apply a knot to a suture. The first actuator 120 can be in an undeployed or extended position with the first spring 123 pushing a portion of the first actuator outward from the outer housing 110. The gear rack 160, the drum or knob 150, which is not rotatable as described above, the actuator shaft 140, and the pusher rod 210 can be at their proximalmost or retracted position. The second actuator 130 can be at its distalmost position (e.g., generally extending away from the outer housing 110). As described above, the user can view the position of the gear rack 160, and at least a portion of the drum or knob 150, and optionally a portion of the actuator shaft 140 from the aperture 116 of the outer housing 110.

Figure 8B:
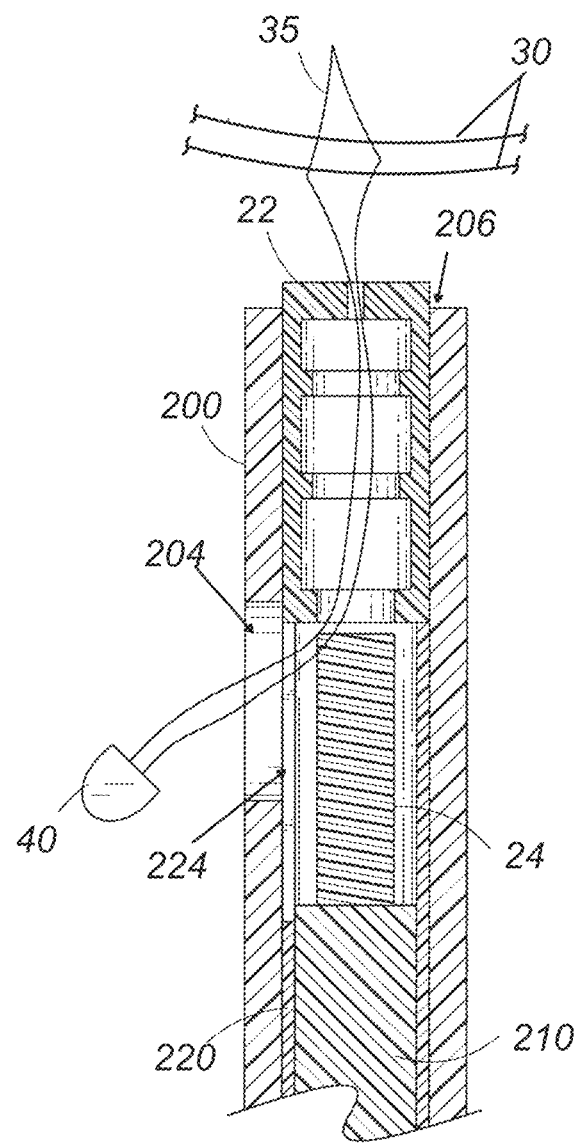
FIGS. 8B and 8C are side cross-sectional views of an example distal portion of a knot placement device at a start of a knot placement procedure.
Figure 8C:
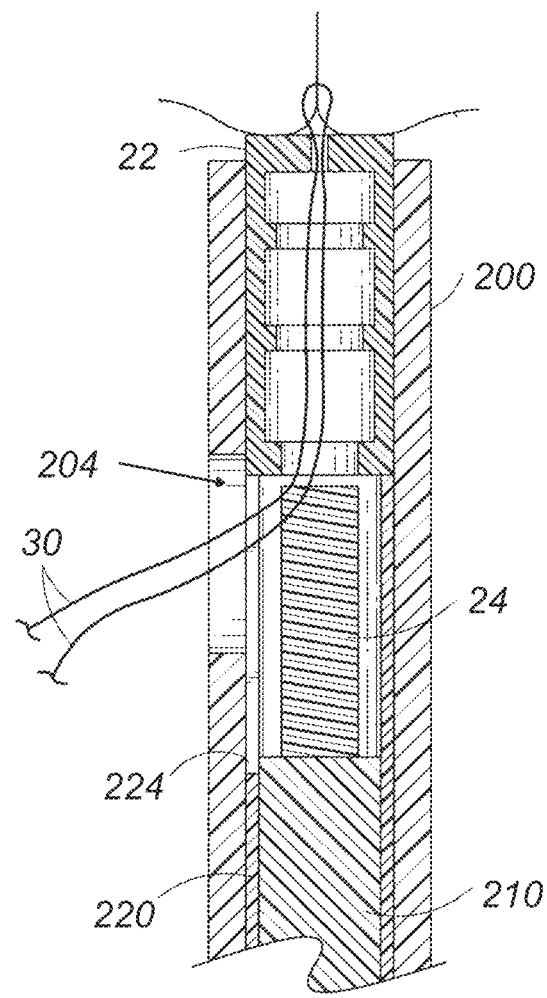

FIG. 8B illustrates the distal portion of the elongate member 200 of the knot placement device 10 housing the pusher rod 210, and an intermediate elongate tube or sleeve 220. Two or more suture portions 30 can be extended through an opening in the distal end 206 of the elongate member 200, and out of an opening 224 in the sleeve 220 and an opening 204 in the distal portion of the elongate member 200 with the use of a threader 35. The suture portions 30 can be passed through a loop of the threader 135 located distal of the distal end 206 of the elongate member 200. The threader 35 can have a tab 40 trailing outside the opening 204. Pulling the tab 40 proximally can dispose the suture portions 30 into the knot placement device 10 as described above. The sleeve 220 can be sized to support a plug 24 of the type disclosed in U.S. Pat. No. 8,469,975, with the suture portions 30 extending through the knot body 22. The plug 24 and the sleeve 220 can be located proximally from the knot body 22. As shown in FIG. 8C, the suture portions 30 can be tightened, by hand or by a device, to close an opening in the tissue.

Figure 9:
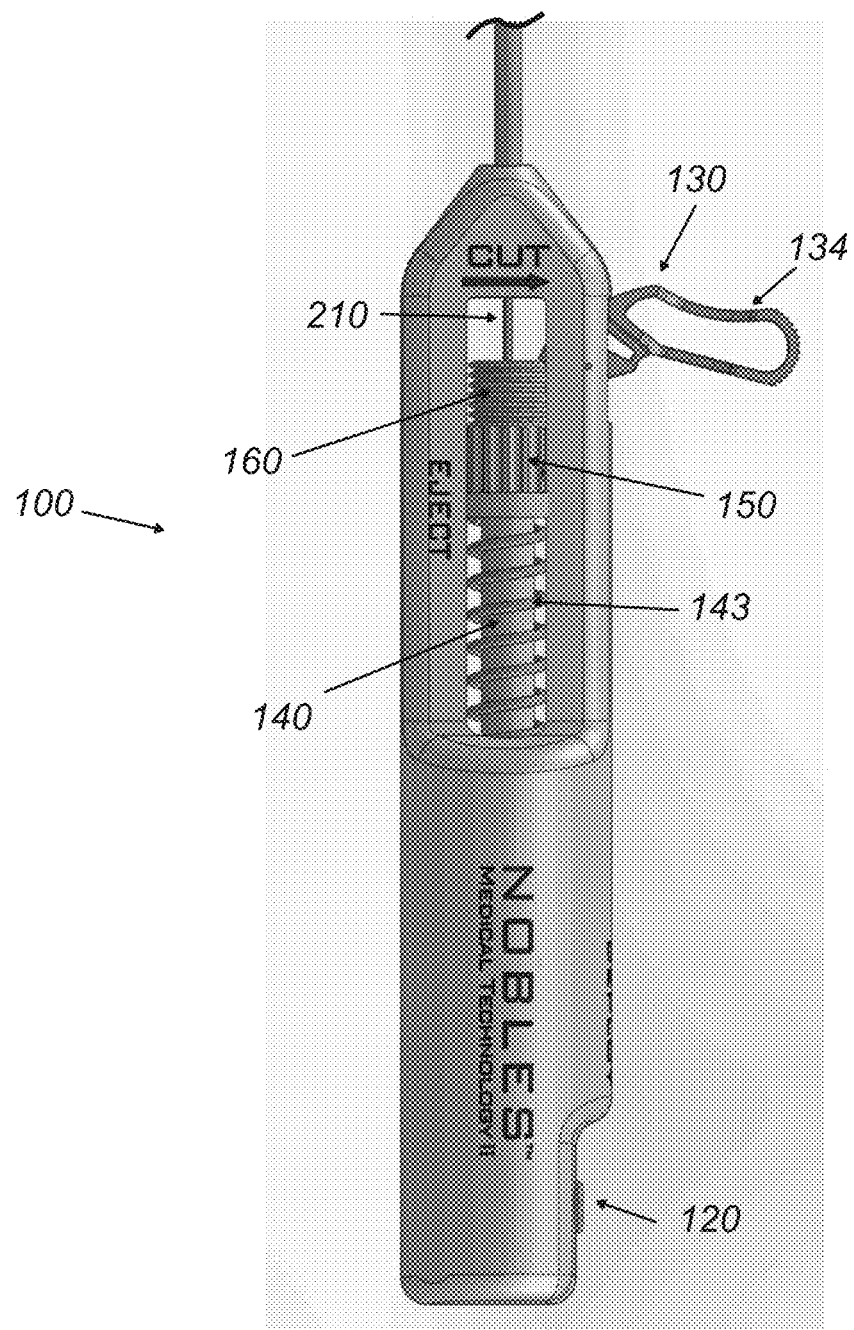
FIG. 9 is a side view of the handle of FIG. 8A after advancing an actuation shaft of the handle.

FIG. 9 illustrates the handle 100 when the first actuator 120 has been deployed, such as being advanced into the outer housing 110, but the knot body 22 and plug 24 has not been released from the knot placement device 10. Specifically, pressing the first actuator 120 into the outer housing 110 of the handle 100 can push the first actuator 120 out of engagement with the actuator shaft 140. With the first actuator 120 no longer holding the actuator shaft 140 at the proximalmost position, the actuator shaft 140 (and the gear rack 160, the drum or knob 150, and the pusher rod 210 that are coupled to the actuator shaft 140) can be advanced distally under the biasing force of the second spring 143.

Figure 10:
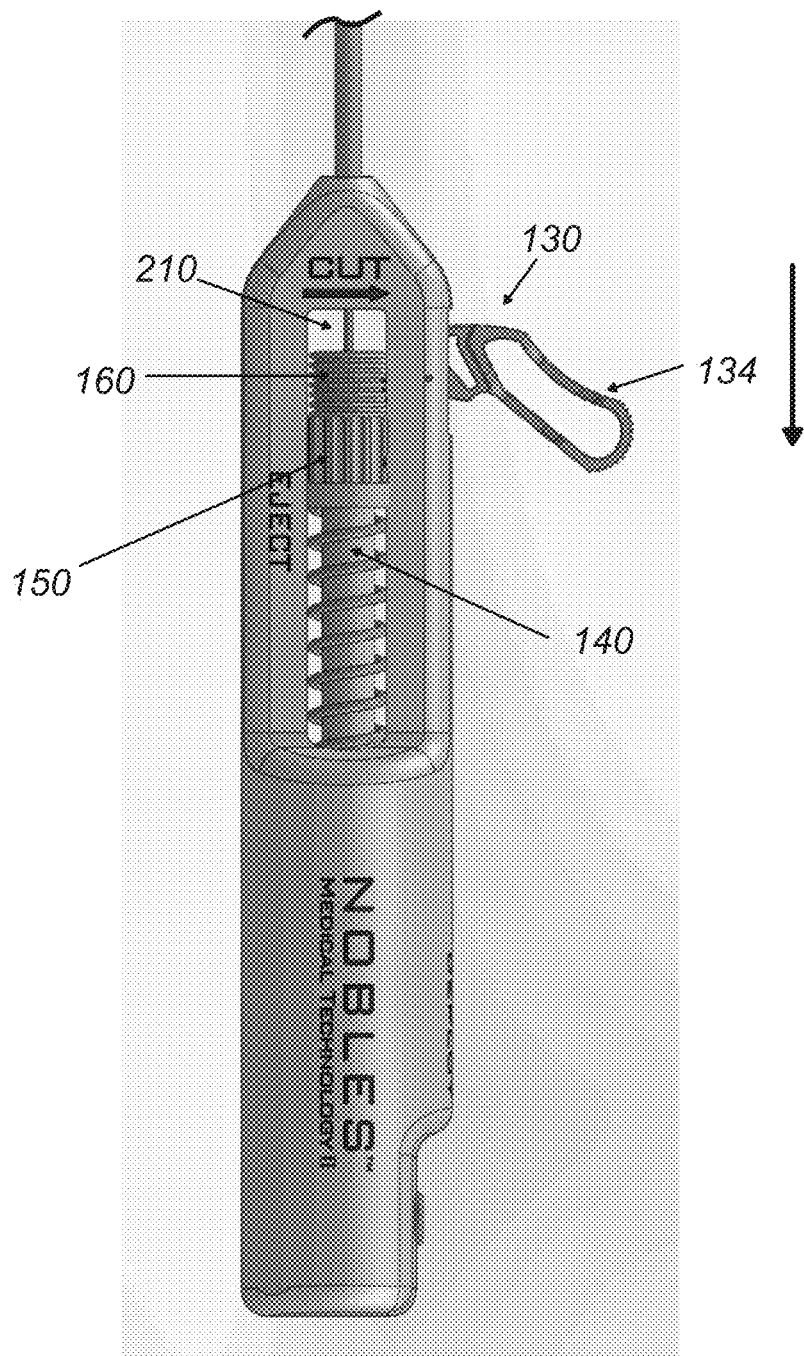
FIG. 10 is a side view of the handle of FIG. 8A when a lever arm of the handle is rotated proximally to an intermediate position.

Turning to FIG. 10, the long arm 134 of the second actuator 130 can be translated proximally such as shown by the arrow, thereby moving the gear rack 160, the rotatable drum or knob 150, the actuator shaft 140, and the pusher rod 210 further distally. Turning to FIG. 11, the long arm 134 of the second actuator 130 has reached its proximalmost position. In some embodiments, the proximalmost position can be reached when the long arm 134 contacts an outer wall of the outer housing 110. Correspondingly, the gear rack 160, the rotatable knob or drum 150, the actuator shaft 140, and the pusher rod 210 can be at their distalmost, or fully deployed position. The distalmost or fully deployed position can be reached when the gear rack 160 contacts an internal transverse wall of the outer housing 110 near its distal end 112. This proximalmost position of the second actuator 130 can be reached upon application of the first actuator 120, which can properly release of the knot body 22 and the plug 24, and no further movement of the second actuator 130 by the user may be needed to deploy the knot 20. This position can also be achieved manually by the user when the application of the first actuator 120 fails to properly deploy the knot 20. For example, pressing the first actuator 120 only partially ejects the knot from the knot placement device 10.

Figure 12A:
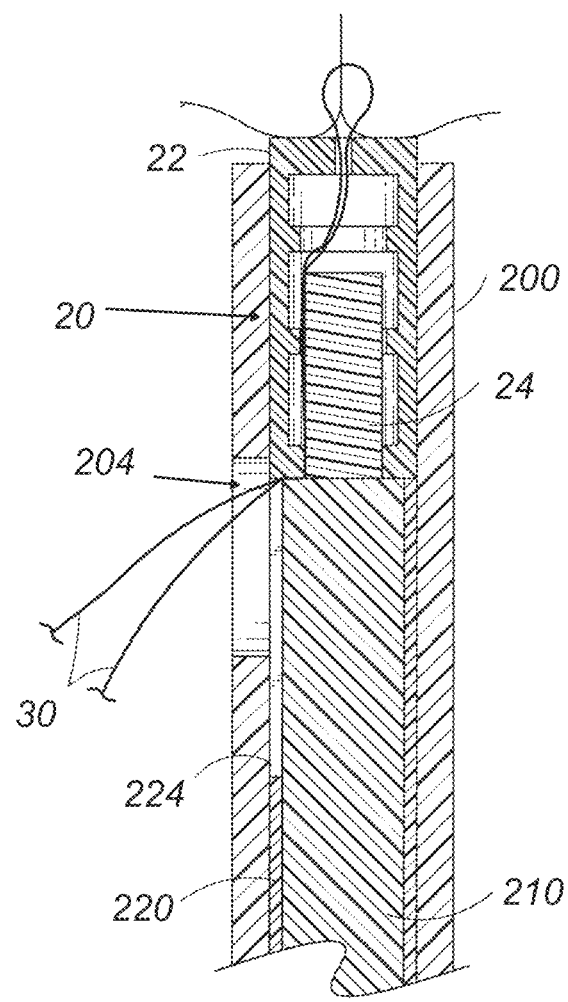
FIG. 12A is a side cross-sectional view of the distal portion of FIG. 8B when a plug is advanced into a knot body.
Figure 12B:
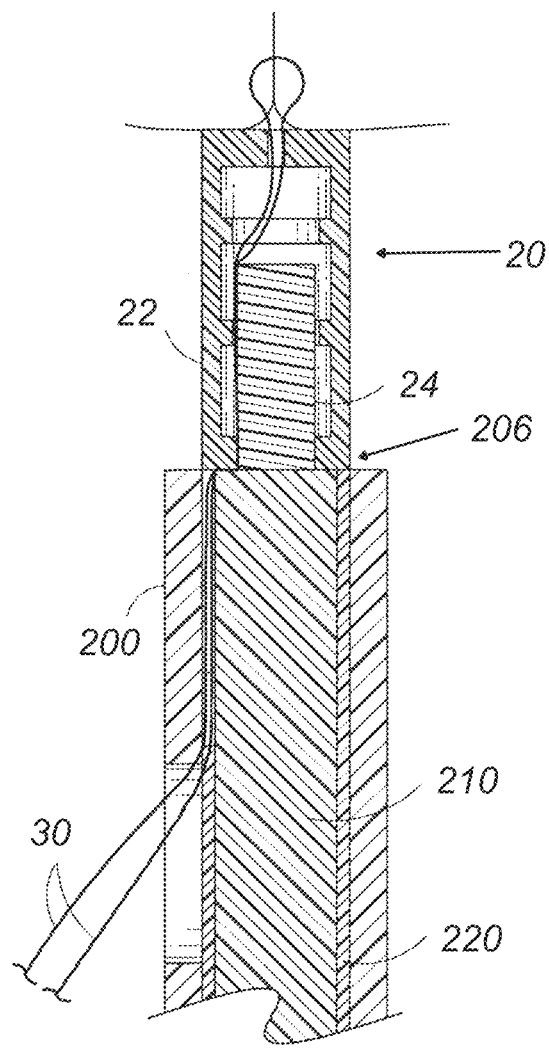
FIG. 12B is a side cross-sectional view of the distal portion of FIG. 8B when the knot of FIG. 12A is ejected from the knot placement device.
Figure 12C:
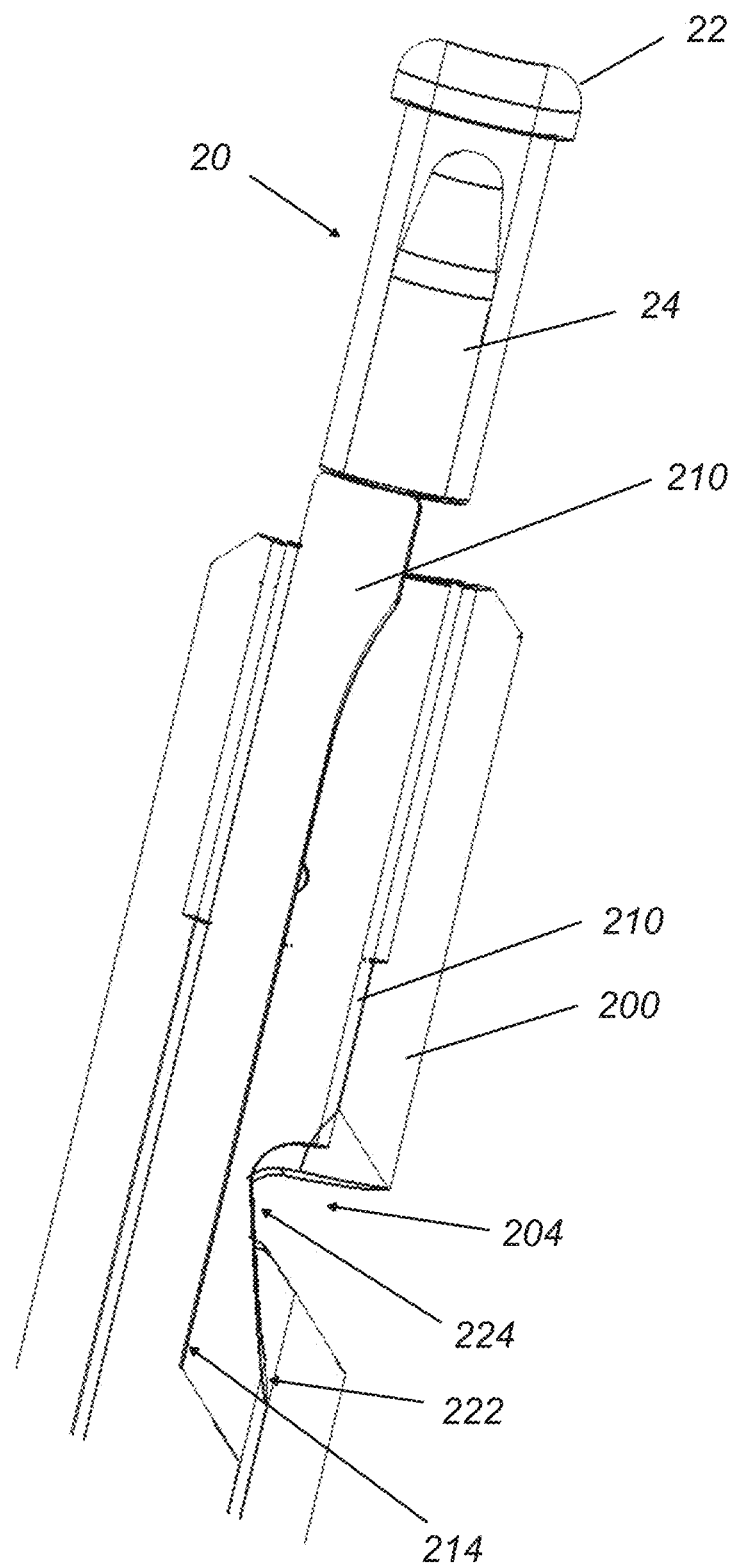
FIG. 12C is a perspective cross-sectional view of a distal portion of the knot placement device of FIG. 2 with suture portions and a threader hidden for clarity.

FIG. 12A illustrates the distal portion of the knot placement device 10 when the pusher rod 210 has distally advanced the plug 24 into the knot body 22, with the suture portions 30 secured between the knot body 22 and plug 24, but before the knot body 22 and the plug 24 are ejected from the distal end of the elongate member 200. FIGS. 12B and 12C illustrate embodiments of the distal portion of the knot placement device 10 when the formed knot 20 has been ejected substantially completely out of the opening 206 on the distal end of the elongate member 200. As shown in FIGS. 12B and 12C, the sleeve 220 can also be advanced distally by application of the first actuator 120 and/or the second actuator 130. In some embodiments, the sleeve 220 can extend proximally into the handle 100. The sleeve 220 can extend proximal of the mounting hub 202 (FIG. 3C) when the actuator shaft 140 and the pusher rod 210 are at the proximalmost position. Unlike the pusher rod 210, the sleeve 220 can be uncoupled from the actuator shaft 140. When advanced distally, a distal surface of the gear track 160 can contact a proximal end of the sleeve 220 inside the handle 100 and can push the sleeve 220 distally.

Figure 13A:
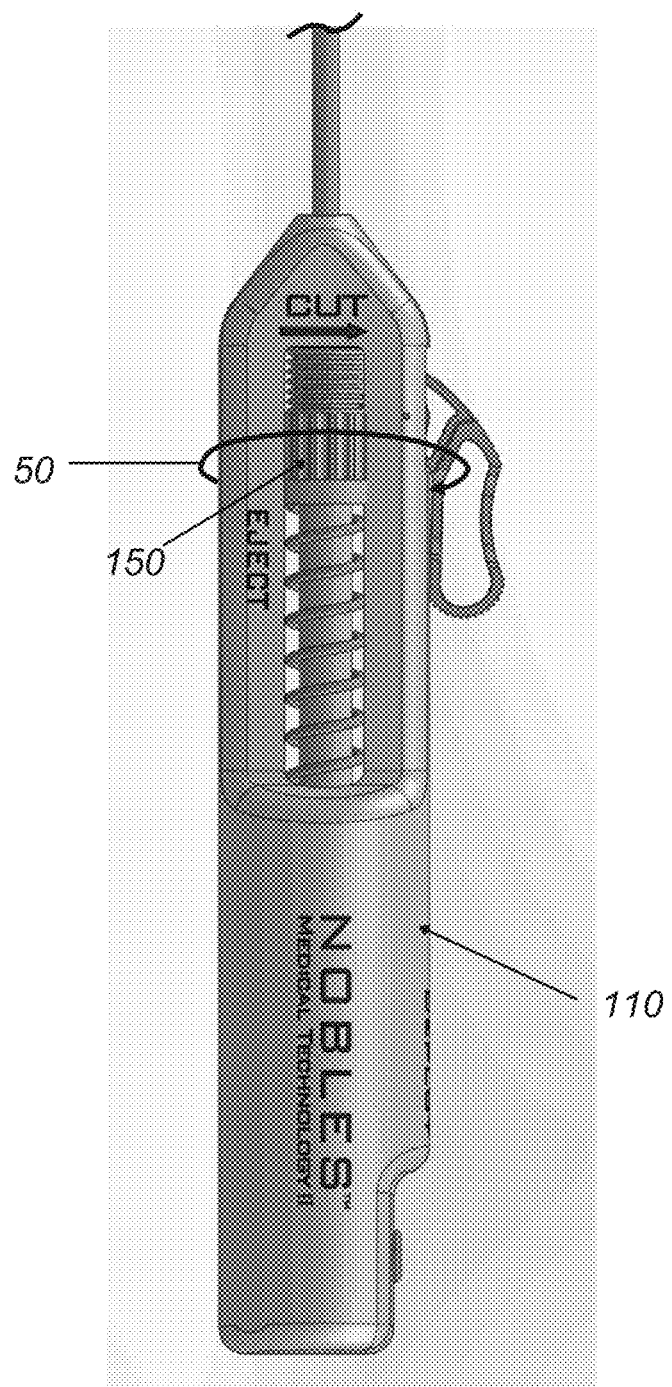
FIG. 13A is a side view of the handle of FIG. 8A when a rotatable knob is rotated as shown by the arrow.
Figure 13B:
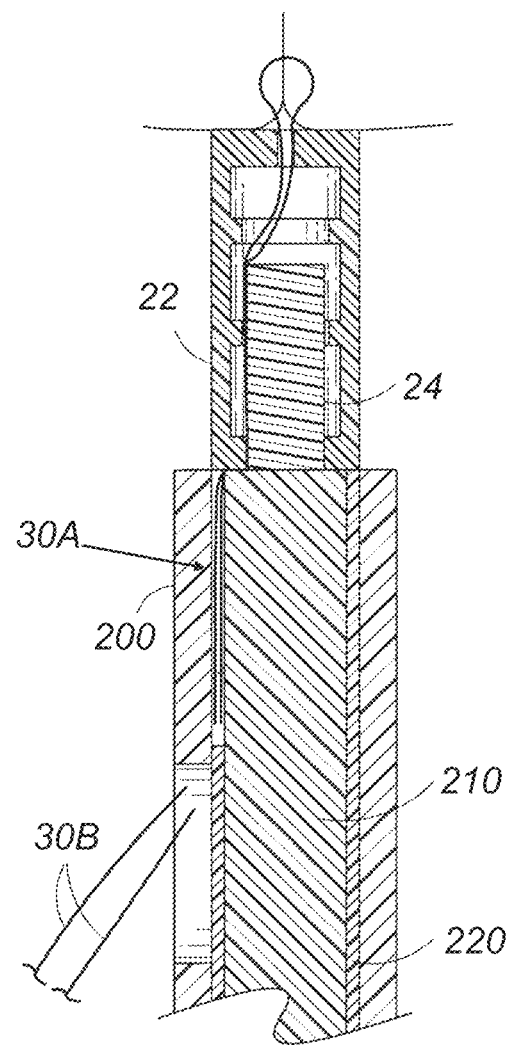
FIG. 13B is a side cross-sectional view of the distal portion of FIG. 8B when suture portions are cut.
Figure 13C:
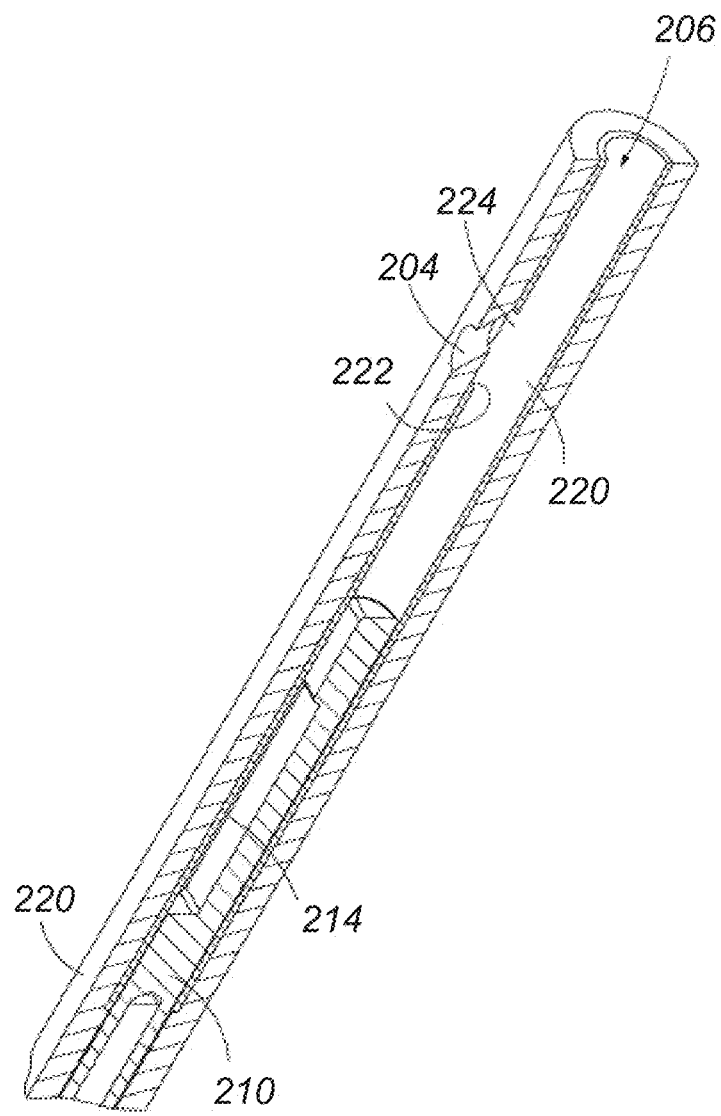
FIG. 13C is a perspective cross-sectional view of a distal portion of an example knot placement device with the knot hidden for clarity.

Turning to FIG. 13A, the rotatable drum or knob 150 can then be rotated about the longitudinal axis of the outer housing 110, in a first direction such as indicated by the arrow 50, from a resting position to a rotated position. The first direction can be clockwise or counterclockwise. As described above, the rotatable drum or knob 150 can be maintained in place upon release by the user, even when the user has not rotated the drum or knob 150 to the fullest extent. Specifically, the handle 100 can include a friction surface, such as a living hinge, a ball detent, a leaf spring, and the like described above, which can impart a frictional force against the drum or knob 150 rotating in a reverse direction toward its resting position. The user can release a force on the drum or knob 150 applied by the user's hand temporarily. The user can then resume further rotating the drum or knob 150 by turning the drum or knob 150 with a force that overcomes the frictional force. As shown in FIG. 13B, rotation of the pusher rod 210 can cause a cutting edge 214 (shown in FIGS. 12C and 13C) near a tip of the pusher rod 210 to rotate toward the opening 224 (shown in FIGS. 12C and 13C) in the sleeve 220. The opening 224 can have a cutting edge 222 (shown in FIGS. 12C and 13C) that cooperates with the cutting edge 214 of the pusher rod 210 to cut the suture portions 30A, 30B. In some embodiments, the opening 204 of the elongate member 200 can have a cutting edge that cooperates with the cutting edge 214 of the pusher rod 210 to cut the suture 30.

Figure 14A:
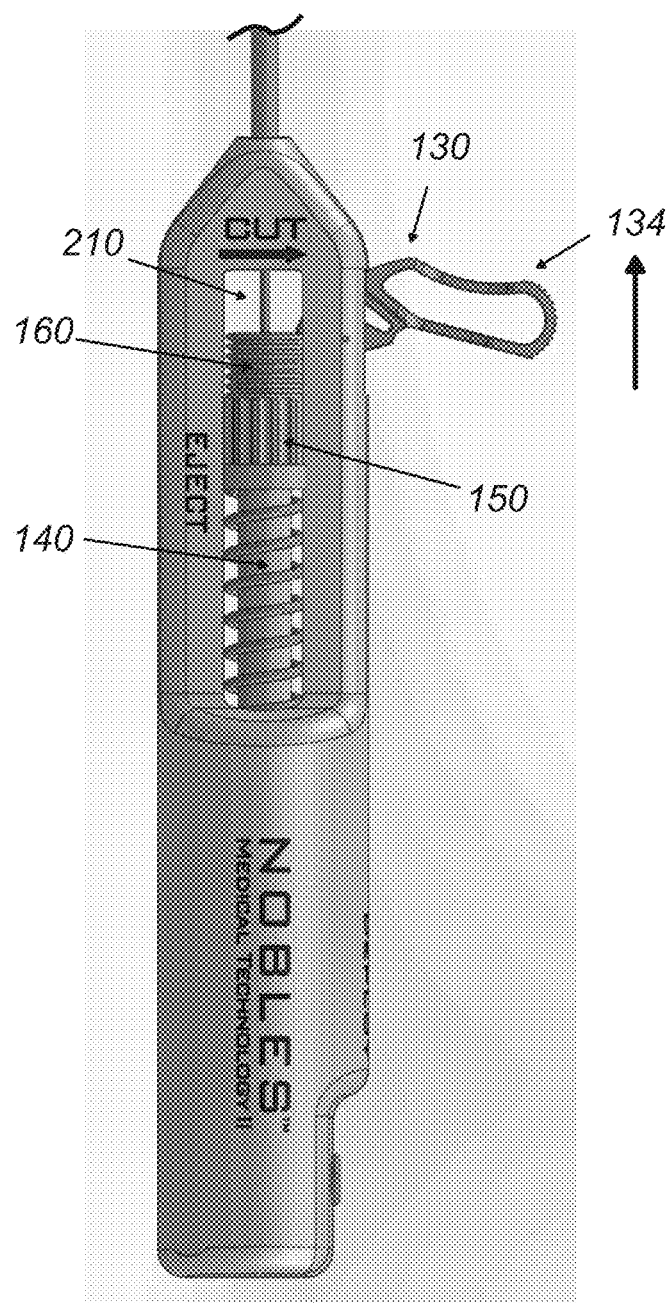
FIG. 14A is a side view of the handle of FIG. 8A when the lever arm of the handle is rotated back to a distal position.
Figure 14B:
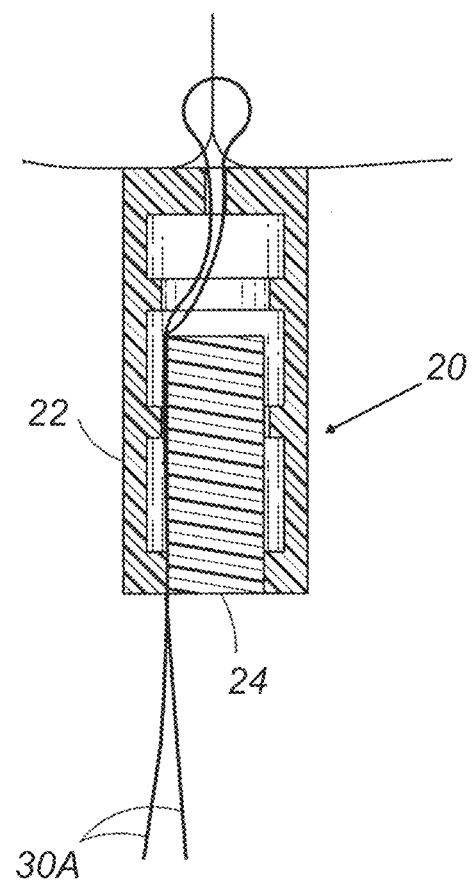
FIG. 14B is a side cross-sectional view of the distal portion of FIG. 8B when the cut suture portions are removed from the knot placement device.

As further shown in FIG. 13B, after the suture portions 30B are cut from the suture portions 30A connected to the knot 20, portion(s) of the suture portions 30A, such as tails of the suture portions 30A, can be stuck within the knot placement device 10, such as between the pusher rod 210 and an inner wall of the elongate member 200. As shown in FIG. 14A, the long arm 134 of the second actuator 130 can be rotated in a distal direction, such as shown by the arrow, toward the distal end 112 of the outer housing 110. Moving the second actuator 130 this way can retract the gear rack 160, the drum or knob 150, the actuator shaft 140, and the pusher rod 210. This can release the portion(s) of suture portions 30A stuck within the knot placement device 10 so that the knot placement device 10 can be withdrawn from the patient's body, leaving the formed knot 20 at the treatment location, as shown in FIG. 14B.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can" or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "about," "generally," and "substantially" as used herein represent a value, amount, or characteristic close to the stated value, amount, or characteristic that still performs a desired function or achieves a desired result. For example, the terms "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A knot placement device for applying a knot to a suture, the device comprising:

an elongate body having a proximal end and a distal end, the elongate body further having a lumen extending from the proximal end to the distal end;

a pusher rod slidably disposed within the elongate body; and a handle coupled to the proximal end of the elongate body, the handle comprising:

an elongate outer housing having a longitudinal axis, the pusher rod extending distally from the elongate outer housing and connected to an actuator shaft within the elongate outer housing, a first actuator with at least a portion extending outside the outer housing, wherein activating the first actuator is configured to advance the pusher rod of the knot placement device distally, a second actuator operably coupled to the actuator shaft, the second actuator configured to be translated to further advance the actuator shaft and push rod distally and to retract the actuator shaft and pusher rod proximally, a knob configured to be rotatable about the longitudinal axis, the outer housing having an aperture configured to allow a user to rotate the knob to cut the suture by rotating a cutting surface of the knot placement device, the knob having a resting position, and a friction mechanism operably coupled to the knob and imparting a force against the knob returning to the resting position when a user rotates the knob about the longitudinal axis in a first direction, wherein the friction mechanism prevents motion other than in the first direction, wherein advancing the pusher rod distally is configured to form a knot by advancing a plug into a knot body positioned within the elongate body to secure the suture therebetween and to eject the knot from the elongate body, and wherein retracting the pusher rod proximally is configured to release the cut suture.

2. The device of claim 1, wherein the friction mechanism comprises a ratcheting mechanism.

3. The device of claim 1, wherein the friction mechanism comprises a ball detent or a living hinge and the knob comprises a plurality of grooves around a circumference of the knob and substantially along the longitudinal axis.

4. The device of claim 1, wherein the friction mechanism comprises a leaf spring pressed against the knob.

5. The device of claim 1, wherein the friction mechanism makes contact with the knob when the first actuator is advanced into the outer housing.

6. The device of claim 1, wherein the friction mechanism is configured to impart the frictional force against the knob returning to the resting position until the user overcomes the frictional force by further rotating the knob in the first direction.

7. The device of claim 1, wherein the second actuator comprises at least one tooth configured to mate with at least one rib on the actuator shaft transverse to the longitudinal axis, wherein the mating of the at least one tooth and at least one rib allows movements of the second actuator to translate to linear movements of the actuator shaft.

8. The device of claim 1, wherein the second actuator comprises a lever arm having a long arm and a short arm divided by a pivot point, wherein the long arm is configured to rotate proximally to further advance the actuator shaft distally and to rotate distally to retract the actuator shaft proximally.

9. The device of claim 8, wherein the long arm is at a distalmost position at a start of a knot placement procedure.

10. The device of claim 8, wherein the short arm comprises a plurality of teeth and the actuator shaft comprises a gear rack, wherein the plurality of teeth mesh with teeth of the gear rack when the lever arm is rotated about the pivot point.

11. The device of claim 10, wherein the gear rack and the knob comprise a single-piece structure.

12. The device of claim 1, wherein the knob is spring-biased onto the friction mechanism.

13. The device of claim 1, wherein the knob is not rotatable until the actuator shaft is advanced by deploying the first actuator.

14. The device of claim 1, wherein the knob is coupled to the actuator shaft.

15. The device of claim 14, wherein an internal wall of the outer housing comprises a segment of partitions extending generally along the longitudinal axis, the actuator shaft comprising a pin extending transverse to the longitudinal axis and a space between two adjacent partitions configured to accommodate the pin to resist rotation of the actuator shaft and the knob.

16. The device of claim 15, wherein the pin moves to be distal of the segment of partitions after deploying the first actuator into a segment of the outer housing having an inner compartment dimensioned to allow rotation of the pin about the longitudinal axis.

17. The device of claim 1, wherein the actuator shaft is spring-loaded such that advancing the first actuator into the outer housing causes the actuator shaft to spring distally from a retracted position.

18. The device of claim 1, wherein the plug is positioned proximal of the knot body when undeployed.

19. A method of applying a knot to two or more suture portions using a knot placement device, the knot comprising a knot body and a plug configured to secure the suture portions therebetween, the knot placement device comprising a handle and an elongate shaft extending distally from the handle, the method comprising:

advancing a distal portion of the knot placement device to a location near tissue adjacent an opening, wherein the two or more suture portions are positioned within a knot body located in the distal portion, the distal portion further comprising a plug slidably disposed therein proximal to the knot body;

actuating a first actuator of the handle to advance the plug toward the knot body to fixedly secure the two or more suture portions between the knot body and an outer surface of the plug by pushing the plug using a pusher rod, the pusher rod operably coupled to the first actuator;

actuating a second actuator of the handle to further distally advance the pusher rod to eject the plug and knot body fixedly securing the two or more suture portions from the distal portion of the knot placement device; and rotating in a first direction a rotatable knob about a longitudinal axis of the handle to rotate a cutting surface of the knot placement device to cut the suture portions, wherein the knob is configured to remain in place upon release by a user.

20. The method of claim 19, wherein translating the second actuator further comprises advancing the cutting surface distally.

* * * * *